United States Patent
Marceles Palma et al.

(10) Patent No.: US 8,883,680 B2
(45) Date of Patent: Nov. 11, 2014

(54) HERBICIDE COMBINATIONS WITH PARTICULAR SULPHONYL UREAS

(75) Inventors: Victor Jose Marceles Palma, Düsseldorf (DE); Allan Eadie, Düsseldorf (DE); Udo Bickers, Kelkheim (DE)

(73) Assignee: Bayer Cropscience AG, Monheim (DE)

( * ) Notice: Subject to any disclaimer, the term of this patent is extended or adjusted under 35 U.S.C. 154(b) by 857 days.

(21) Appl. No.: 12/514,441

(22) PCT Filed: Oct. 27, 2007

(86) PCT No.: PCT/EP2007/009345
§ 371 (c)(1),
(2), (4) Date: Sep. 29, 2009

(87) PCT Pub. No.: WO2008/058622
PCT Pub. Date: May 22, 2008

(65) Prior Publication Data
US 2010/0041553 A1    Feb. 18, 2010

(30) Foreign Application Priority Data

Nov. 13, 2006    (EP) .................................... 06023578

(51) Int. Cl.
A01N 43/54    (2006.01)
A01N 25/32    (2006.01)
A01N 59/00    (2006.01)
A01N 47/36    (2006.01)

(52) U.S. Cl.
CPC ...................................... A01N 47/36 (2013.01)
USPC ............................. 504/103; 504/136; 504/124

(58) Field of Classification Search
None
See application file for complete search history.

(56) References Cited

U.S. PATENT DOCUMENTS

| | | | |
|---|---|---|---|
| 4,400,196 A | 8/1983 | Albrecht et al. | |
| 4,443,971 A | 4/1984 | Chaleff | |
| 4,601,747 A | 7/1986 | Willms et al. | |
| 4,623,727 A | 11/1986 | Hubele | |
| 4,639,266 A | 1/1987 | Heubach et al. | |
| 4,718,937 A | 1/1988 | Willms et al. | |
| 4,761,373 A | 8/1988 | Anderson et al. | |
| 4,881,966 A | 11/1989 | Nyffeler et al. | |
| 4,902,340 A | 2/1990 | Hubele | |
| 5,013,659 A | 5/1991 | Bedbrook et al. | |
| 5,162,602 A | 11/1992 | Somers et al. | |
| 5,236,887 A | 8/1993 | Noveroske | |
| 6,096,687 A | 8/2000 | Parrish | |
| 6,455,470 B1 | 9/2002 | Parrish | |
| 2003/0050193 A1* | 3/2003 | Bieringer et al. | 504/136 |
| 2003/0181333 A1 | 9/2003 | Hacker et al. | |

FOREIGN PATENT DOCUMENTS

| | | | |
|---|---|---|---|
| CA | 1288253 C | 9/1991 | |
| EP | 0333131 A1 | 3/1989 | |
| EP | 0346620 A1 | 5/1989 | |
| EP | 0269806 B1 | 2/1991 | |
| EP | 0193259 B1 | 12/1991 | |
| EP | 0492366 B1 | 12/1991 | |
| EP | 0142924 B1 | 4/1992 | |
| EP | 0131624 B1 | 9/1992 | |
| EP | 0221044 B1 | 9/1992 | |
| EP | 0336151 B1 | 3/1993 | |
| EP | 0582198 B1 | 7/1993 | |
| EP | 0502014 B1 | 2/1995 | |
| EP | 0257993 B1 | 11/1996 | |
| EP | 0476555 B1 | 12/1998 | |
| WO | 91/07874 A1 | 6/1991 | |
| WO | 91/08202 A1 | 6/1991 | |
| WO | 91/13972 A1 | 9/1991 | |

(Continued)

OTHER PUBLICATIONS

Domaradzki, K. Pamietnik Pulawski, 1999, v. 118, pp. 99-120. English translation also enclosed.*

(Continued)

Primary Examiner — Mina Haghighatian
Assistant Examiner — Erin Hirt
(74) Attorney, Agent, or Firm — Miles & Stockbridge P.C.

(57) ABSTRACT

Herbicide combinations comprising components (A) and (B) show improved herbicidal effects:
(A) one or more herbicides from the group of the compounds of the formula (I) and their salts,

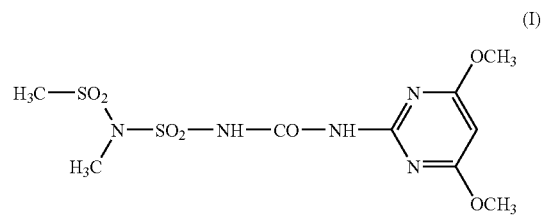

and
(B) one or more herbicides from the group of the compounds of the formula (II) and their salts and esters,

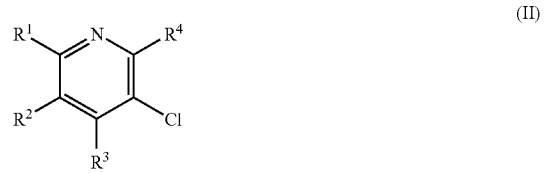

in which
$R^1$=is fluorine or chlorine,
$R^2$=is H or chlorine,
$R^3$=is H or $NH_2$, and
$R^4$=is COOH, $OCH_2COOH$, $OCH_2COOCH(CH_3)CH_2O(CH_2)_3CH_3$ or $OCH_2COOCH(CH_3)(CH_2)_5CH_3$,
where at least one of the radicals $R^2$ and $R^3$ is different from H.

20 Claims, No Drawings

(56) References Cited

FOREIGN PATENT DOCUMENTS

| WO | 91/19806 A1 | 12/1991 | | |
| WO | 92/11376 A1 | 7/1992 | | |
| WO | 92/14827 A1 | 9/1992 | | |
| WO | 95/07897 A1 | 3/1995 | | |
| WO | WO02078442 | * | 10/2002 | ............ A01N 25/04 |
| WO | 2004/080182 A2 | 9/2004 | | |

OTHER PUBLICATIONS

Grodyl 75 WG data sheet. http://www.bayercropscience.pl/strony/1/i/40.php?product_id=77. Available for sale at least since 1999.*

International Search Report for PCT/EP07/09345, dated Sep. 8, 2008.

* cited by examiner

HERBICIDE COMBINATIONS WITH PARTICULAR SULPHONYL UREAS

CROSS REFERENCE TO RELATED APPLICATIONS

This application is a §371 National Stage Application of PCT/EP07/09345 filed Oct. 27, 2007 which claims priority to European Application 06023578.5 filed Nov. 13, 2006.

BACKGROUND OF THE INVENTION

1. Field of the Invention

The invention is in the technical field of crop protection products which can be employed against harmful plants, for example in crop plants, and which comprise, as active compounds, a combination of at least two specific herbicides.

2. Description of Related Art

The document EP-A-131258 discloses sulfonylureas and their salts and also their use as herbicides and/or plant growth regulators.

The efficacy of these herbicides against harmful plants in the crop plants is at a high level, but depends in general on the application rate, the formulation in question, the harmful plants or spectrum of harmful plants to be controlled in each case, the climatic conditions, the soil conditions and the like. Another criterion is the duration of action, or the breakdown rate of the herbicide. If appropriate, changes in the sensitivity of harmful plants, which may occur upon prolonged use of the herbicides or within geographic limitations, must also be taken into consideration. The compensation of losses in action in the case of individual harmful plants by increasing the application rates of the herbicides is only possible to a certain degree, for example because such a procedure frequently reduces the selectivity of the herbicides or because the action is not improved, even when applying higher rates. In some cases, the selectivity in crops can be improved by adding safeners. In general, however, there remains a need for methods to achieve the herbicidal action with a lower application rate of active compounds. Not only does a lower application rate reduce the amount of an active compound required for application, but, as a rule, it also reduces the amount of formulation auxiliaries required. It both reduces the economic input and improves the ecological compatibility of the herbicide treatment.

One possibility of improving the application profile of a herbicide can consist in combining the active compound with one or more other active compounds. However, the combined use of a plurality of active compounds frequently causes phenomena of physical and biological incompatibility, for example a lack of stability in a coformulation, decomposition of an active compound, or antagonism of the active compounds. What is desired are, in contrast, combinations of active compounds having an advantageous activity profile, high stability and, if possible, a synergistically improved action, which allows the application rate to be reduced in comparison with the individual application of the active compounds to be combined.

SUMMARY OF THE INVENTION

Surprisingly, it has now been found that certain active compounds from the group of the sulfonylureas or their salts in combination with certain structurally different herbicides act together in a particularly advantageous manner, for example when they are employed in crop plants.

The invention thus provides herbicide combinations comprising components (A) and (B), where
(A) denotes one or more herbicides of the formula (I) and their salts

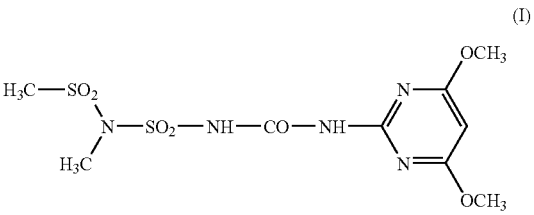 [SMILES: COc1cc(OC)nc(NC(=O)NS(=O)(=O)N(C)S(C)(=O)=O)n1]

and
(B) denotes one or more herbicides selected from the group of the compounds of the formula (II) and their salts and esters,

in which
$R^1$ = is fluorine or chlorine,
$R^2$ = is H or chlorine,
$R^3$ = is H or $NH_2$, and
$R^4$ = is COOH, $OCH_2COOH$, $OCH_2COOCH(CH_3)CH_2O(CH_2)_3CH_3$ or $OCH_2COOCH(CH_3)(CH_2)_5CH_3$,
where at least one of the radicals $R^2$ and $R^3$ is different from H.

DETAILED DESCRIPTION OF A PREFERRED EMBODIMENT

Preferred compounds of the formula (II) are (listed with the "common name" and a literature reference, for example from "The Pesticide Manual" 14th Ed., British Crop Protection Council 2006, abbreviated as "PM")

(B1) picloram, in particular also including its salts and esters (PM, pp. 838-840), for example 4-amino-3,5,6-trichloro-pyridine-2-carboxylic acid (application rate generally: 20-300 g of AS/ha, preferably 50-150 g of AS/ha; application rate ratio A:B generally =1:1-1:50, preferably 1:2-1:10);

(B2) aminopyralid, in particular also including its salts and esters (PM, pp. 30-31), for example 4-amino-3,6-dichloropyridine-2-carboxylic acid (application rate generally: 10-200 g of AS/ha, preferably 30-70 g of AS/ha; application rate ratio A:B generally =1:1-1:20, preferably 1:1-1:5);

(B3) triclopyr, in particular also including its salts and esters (PM, pp. 1068-1069), for example 3,5,6-trichloro-2-pyridyloxyacetic acid (application rate generally: 50-300 g of AS/ha, preferably 100-200 g of AS/ha; application rate ratio A:B generally =1:1-1:20, preferably 1:2-1:10);

(B4) fluoroxypyr, in particular also including its salts and esters (PM, pp. 509-511) for example 4-amino-3,5-dichloro-6-fluoro-2-pyridylacetic acid (application rate generally: 50-300 g of AS/ha, preferably 100-200 g of AS/ha; application rate ratio A:B generally =1:1-1:20, preferably 1:2-1:10.

Preferred mixing partners (B) are picloram (B1.1), picloram-dimethylammonium (B1.2), picloram-isoctyl (B1.3), picloram-sodium (B1.4), picloram-potassium (B1.5), picloram-triisopropanolammonium (B1.6), picloram-triethanolammonium (=picloram-trolamine) (B1.7), picloram-triisopropylammonium (B1.8), aminopyralid (B2.1), aminopyralid-sodium (B2.2), aminopyralid-potassium (B2.3), aminopyralid-tri(2-hydroxypropyl)ammonium (B2.4), triclopyr (B3.1), triclopyr-butotyl (B3.2), triclopyr-triethylammonium (B3.3), fluoroxypyr (B4.1), fluoroxypyr-2-butoxy-1-methylethyl (B4.2), fluoroxypyr-1-methylheptyl (B4.3).

The herbicide combinations according to the invention comprise a herbicidally effective amount of components (A) and (B) and may comprise further components, for example agrochemically active compounds of a different type and/or formulation auxiliaries and/or additives customary in crop protection, or they may be employed together with these.

In a preferred embodiment, the herbicide combinations according to the invention have synergistic effects. The synergistic effects can be observed, for example, when the active compounds (A) and (B) are applied together, but they can frequently also be observed when the compounds are applied as a split application over time. Another possibility is the application of the individual herbicides or the herbicide combinations in a plurality of portions (sequential application), for example after pre-emergence applications, followed by post-emergence applications or after early post-emergence applications, followed by applications at medium or late post-emergence. Preferred is the simultaneous or nearly simultaneous application of the active compounds of the herbicide combination according to the invention.

The synergistic effects allow the application rates of the individual active compounds to be reduced, a more potent action at the same application rate, the control of hitherto uncontrollable species (activity gaps), an extended application period and/or a reduced number of individual applications required and—as a result for the user—more advantageous weed control systems both from an economical and ecological point of view.

The abovementioned formulae (I) and (III) include all stereoisomers and their mixtures, in particular also racemic mixtures and—if enantiomers are possible—the respective biologically active enantiomer. The compounds of the formulae (I) and (II) are capable of forming salts, for example, in which a hydrogen atom is replaced by an agriculturally suitable cation. These salts are, for example, metal salts, in particular alkali metal salts or alkaline earth metal salts, in particular sodium and potassium salts, or else ammonium salts or salts with organic amines. Salt formation may also take place by addition of an acid to basic groups, such as, for example, amino and alkylamino. Acids suitable for this purpose are strong inorganic and organic acids, for example HCl, HBr, $H_2SO_4$ or $HNO_3$. Compounds of the formula (I) and their salts and also their preparation are described, for example, in EP-A-131258 and U.S. Pat. No. 4,718,937. Preferred compounds of the formula (I) and their salts are 1-(4,6-dimethoxypyrimidin-2-yl)-3-mesyl(methyl)sulfamoylurea (amidosulfuron, A1.1) and its sodium salt (A1.2) (see, for example, EP-A-131258 and PM, pp. 27-28).

The abovementioned active compounds of the formula (I) and their salts are capable of inhibiting the enzyme acetolactate synthase (ALS) and thus protein synthesis in plants. The application rate of the active compounds of the formula (I) and their salts can be varied within a wide range, for example between 1 g and 500 g of AS/ha (AS/ha means "active substance per hectare", based on 100% active compound). In the case of applications at application rates of from 10 g to 300 g of AS/ha of the active compounds of the formula (I) and their salts, preferably the active compounds (A1.1), (A1.2), a relatively broad spectrum of harmful plants is controlled pre- and post-emergence. In the combinations according to the invention, the application rates are generally lower, for example in the range from 0.5 to 200 g of AS/ha, preferably from 1 to 120 g of AS/ha.

If, in the context of this description, the short form of the "common name" of an active compound is used, this embraces all customary derivatives, such as the esters and salts, and isomers, in particular optical isomers, in particular the commercial form or forms, unless the context indicates otherwise. Also included in the case of sulfonamides such as sulfonylureas are salts which are formed by exchanging a hydrogen atom at the sulfonamide group by a cation.

Of particular interest are herbicide combinations according to the invention having a content of the following compounds (A)+(B):

(A1.1)+(B1.1), (A1.1)+(B1.2), (A1.1)+(B1.3), (A1.1)+(B1.4), (A1.1)+(B1.5), (A1.1)+(B1.6), (A1.1)+(B1.7), (A1.1)+(B1.8), (A1.1)+(B2.1), (A1.1)+(B2.2), (A1.1)+(B2.3), (A1.1)+(B2.4), (A1.1)+(B3.1), (A1.1)+(B3.2), (A1.1)+(B3.3), (A1.1)+(B4.1), (A1.1)+(B4.2), (A1.1)+(B4.3);

(A1.2)+(B1.1), (A1.2)+(B1.2), (A1.2)+(B1.3), (A1.2)+(B1.4), (A1.2)+(B1.5), (A1.2)+(B1.6), (A1.2)+(B1.7), (A1.2)+(B1.8), (A1.2)+(B2.1), (A1.2)+(B2.2), (A1.2)+(B2.3), (A1.2)+(B2.4), (A1.2)+(B3.1), (A1.2)+(B3.2), (A1.2)+(B3.3), (A1.2)+(B4.1), (A1.2)+(B4.2), (A1.2)+(B4.3).

It may be advantageous to combine one or more compounds (A) with a plurality of compounds (B), or to combine a plurality of compounds (A) with one or more compounds (B). Furthermore, the combinations according to the invention may comprise agrochemically active compounds of a different structure (active compounds (C)), for example from the group of the safeners, fungicides, herbicides, insecticides and plant growth regulators or formulation auxiliaries and additives customary in crop protection, or they may be used together with these. For such combinations, the preferred conditions illustrated below in particular for combinations (A)+(B) according to the invention also primarily apply, provided they comprise the combinations (A)+(B) according to the invention, and with respect to the combination (A)+(B) in question. Additives are, for example, fertilizers and colorants. Preferred agrochemically active compounds (C) are herbicides and/or safeners.

For use of the herbicide combination according to the invention in plant crops, it may be expedient, depending on the plant crop, to apply a safener (C) from certain application rates upward in order to reduce or to avoid possible damage to the crop plant. The following groups of compounds are examples of suitable safeners (C):

a) Compounds of the dichlorophenylpyrazoline-3-carboxylic acid (S1) type, preferably compounds such as ethyl 1-(2,4-dichlorophenyl)-5-(ethoxycarbonyl)-5-methyl-2-pyrazoline-3-carboxylate (S1-1, mefenpyr-diethyl), and related compounds as they are described for example in WO 91/07874 and PM (pp. 594-595).

b) Dichlorophenylpyrazolecarboxylic acid derivatives, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-

5-phenylpyrazole-3-carboxylate (S1-5) and related compounds as are described in EP-A-333 131 and EP-A-269 806.

c) Compounds of the triazolecarboxylic acid (S1) type, preferably compounds such as fenchlorazole, i.e. ethyl 1-(2,4-dichlorophenyl)-5-trichloromethyl-(1H)-1,2,4-triazole-3-carboxylate (S1-6) and related compounds (see EP-A-174 562 and EP-A-346 620).

d) Compounds of the 5-benzyl- or 5-phenyl-2-isoxazoline-3-carboxylic acid type or of the 5,5-diphenyl-2-isoxazoline-3-carboxylic acid type, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds as are described for example in WO 91/08202, or of ethyl 5,5-diphenyl-2-isoxazoline-3-carboxylate (S1-9, isoxadifen-ethyl) or n-propyl 5,5-diphenyl-2-isoxazoline-3-carboxylate (S1-10) or ethyl 5-(4-fluorophenyl)-5-phenyl-2-isoxazoline-3-carboxylate (S1-11), as are described in patent application (WO-A-95/07897).

e) Compounds of the 8-quinolinoxyacetic acid (S2) type, preferably 1-methylhex-1-yl (5-chloro-8-quinolinoxy)acetate (S2-1, cloquintocet-mexyl, e.g. PM (pp. 195-196), (1,3-dimethylbut-1-yl) (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminooxy)-1-ethyl (5-chloro-8-quinolinoxy)acetate (S2-8), 2-oxoprop-1-yl (5-chloro-8-quinolinoxy)acetate (S2-9) and related compounds as are described in EP-A-86 750, EP-A-94 349 and EP-A-191 736 or EP-A-0 492 366.

f) Compounds of the (5-chloro-8-quinolinoxy)malonic acid type, preferably compounds such as diethyl (5-chloro-8-quinolinoxy)malonate, diallyl (5-chloro-8-quinolinoxy) malonate, methyl ethyl (5-chloro-8-quinolinoxy)malonate and related compounds as are described in EP-A-0 582 198.

g) Active compounds of the phenoxyacetic acids, phenoxypropionic acids or aromatic carboxylic acids type, such as, for example, 2,4-dichlorophenoxyacetic acid (and esters) (2,4-D), 4-chloro-2-methylphenoxypropionic esters (mecoprop), MCPA or 3,6-dichloro-2-methoxybenzoic acid (and esters) (dicamba).

h) Active compounds of the pyrimidine type, such as, for example, "fenclorim" (PM, pp. 386-387) (=4,6-dichloro-2-phenylpyrimidine), i) active compounds of the dichloroacetamide type, which are frequently used as pre-emergence safeners (soil-acting safeners) such as, for example,
  "dichlormid" (PM, pp. 270-271) (=N,N-diallyl-2,2-dichloroacetamide),
  "AR-29148" (=3-dichloroacetyl-2,2,5-trimethyl-1,3-oxazolidone by Stauffer),
  "benoxacor" (PM, pp. 74-75) (=4-dichloroacetyl-3,4-dihydro-3-methyl-2H-1,4-benzoxazine),
  "APPG-1292" (=N-allyl-N[(1,3-dioxolan-2-yl)methyl] dichloroacetamide by PPG Industries),
  "ADK-24" (=N-allyl-N-[(allylaminocarbonyl)methyl] dichloroacetamide by Sagro-Chem),
  "AAD-67" or "AMON 4660" (=3-dichloroacetyl-1-oxa-3-azaspiro[4,5]decane by Nitrokemia or Monsanto),
  "diclonon" or "ABAS145138" or "ALAB145138" (=(=3-dichloroacetyl-2,5,5-trimethyl-1,3-diazabicyclo[4.3.0] nonane by BASF) and
  "furilazole" or "AMON 13900" (see PM, pp. 482-483) (=(RS)-3-dichloroacetyl-5-(2-furyl)-2,2-dimethyloxazolidone)

j) active compounds of the dichloroacetone derivatives type, such as, for example,
  "AMG 191" (CAS Reg. No. 96420-72-3) (=2-dichloromethyl-2-methyl-1,3-dioxolane by Nitrokemia), k) active compounds of the oxyimino compounds type which are known as seed-dressing materials such as, for example,
  "oxabetrinil" (PM, p. 689) (=(Z)-1,3-dioxolan-2-yl-methoxyimino(phenyl)acetonitrile), which is known as safener in seed dressing to prevent metolachlor damage,
  "fluxofenim" (PM, pp. 467-468) (=1-(4-chlorophenyl)-2,2,2-trifluoro-1-ethanone O-(1,3-dioxolan-2-ylmethyl) oxime, which is known as safener in seed dressing to prevent metolachlor damage, and
  "cyometrinil" or "A-CGA-43089" (PM, p. 983) (=(Z)-cyanomethoxyimino(phenyl)acetonitrile), which is known as safener in seed dressing to prevent metolachlor damage, l) active compounds of the thiazolecarboxylic esters type, which are known as seed-dressing materials, such as, for example,
  "flurazole" (PM, pp. 450-451) (=benzyl 2-chloro-4-trifluoromethyl-1,3-thiazole-5-carboxylate), which is known as safener in seed dressing to prevent alachlor and metolachlor damage, m) active compounds of the naphthalenedicarboxylic acid derivatives type which are known as seed-dressing agents, such as, for example,
  "naphthalic anhydride" (PM, pp. 1009-1010) (=1,8-naphthalenedicarboxylic anhydride), which is known as safener for maize in seed dressing to prevent thiocarbamate herbicide damage, n) active compounds of the chromaneacetic acid derivatives type, such as, for example,
  "ACL 304415" (CAS Reg. No. 31541-57-8) (=2-84-carboxychroman-4-yl)acetic acid by American Cyanamid), o) active compounds which, in addition to a herbicidal action against harmful plants, also have a safener action on crop plants, such as, for example,
  "dimepiperate" or "AMY-93" (PM, pp. 302-303) (=S-1-methyl-1-phenylethyl piperidine-1-carbothioate),
  "daimuron" or "ASK 23" (PM, p. 247) (=1-(1-methyl-1-phenylethyl)-3-p-tolylurea),
  "cumyluron"="AJC-940" (=3-(2-chlorophenylmethyl)-1-(1-methyl-1-phenyl-ethyl)urea, see JP-A-60087254),
  "methoxyphenone" or "ANK 049" (=3,3'-dimethyl-4-methoxy-benzophenone),
  "CSB" (=1-bromo-4-(chloromethylsulfonyl)benzene) (CAS Reg. No. 54091-06-4 by Kumiai).

Preferred herbicides (C) are iodosulfuron and its salts and esters (C1), for example iodosulfuron-methyl-sodium (C1.1), bromoxynil and its salts and esters (C2), for example bromoxynil octanoate (C2.1), bromoxynil heptanoate (C2.2), bromoxynil-sodium (C2.3), bromoxynil-potassium (C2.4), ioxynil and its salts and esters (C3), for example ioxynil-sodium (C3.1), ioxynil octanoate (C3.2), metribuzin (C4), propoxycarbazone and its salts and esters (C5), for example propoxycarbazone-sodium (C5.1), ethofumesate (C6), diflufenican (C7), ethoxysulfuron and its salts and esters (C8), for example ethoxysulfuron (C8.1).

Particularly preferred herbicide combinations of this type are:
(A1.1)+(B1.1)+(C1.1), (A1.1)+(B1.2)+(C1.1), (A1.1)+(B1.3)+(C1.1), (A1.1)+(B1.4)+(C1.1), (A1.1)+(B1.5)+(C1.1), (A1.1)+(B1.6)+(C1.1), (A1.1)+(B1.7)+(C1.1), (A1.1)+(B1.8)+(C1.1), (A1.1)+(B2.1)+(C1.1), (A1.1)+(B2.2)+(C1.1), (A1.1)+(B2.3)+(C1.1), (A1.1)+(B2.4)+(C1.1), (A1.1)+(B3.1)+(C1.1), (A1.1)+(B3.2)+(C1.1), (A1.1)+(B3.3)+(C1.1), (A1.1)+(B4.1)+(C1.1), (A1.1)+(B4.2)+(C1.1), (A1.1)+(B4.3)+(C1.1);
(A1.2)+(B1.1)+(C1.1), (A1.2)+(B1.2)+(C1.1), (A1.2)+(B1.3)+(C1.1), (A1.2)+(B1.4)+(C1.1), (A1.2)+(B1.5)+(C1.1), (A1.2)+(B1.6)+(C1.1), (A1.2)+(B1.7)+(C1.1), (A1.2)+(B1.8)+(C1.1), (A1.2)+(B2.1)+(C1.1), (A1.2)+(B2.2)+(C1.1), (A1.2)+(B2.3)+(C1.1), (A1.2)+(B2.4)+(C1.1), (A1.2)+(B3.1)+(C1.1), (A1.2)+(B3.2)+(C1.1), (A1.2)+(B3.3)+(C1.1), (A1.2)+(B4.1)+(C1.1), (A1.2)+(B4.2)+(C1.1), (A1.2)+(B4.3)+(C1.1);
(A1.1)+(B1.1)+(C2.1), (A1.1)+(B1.2)+(C2.1), (A1.1)+(B1.3)+(C2.1), (A1.1)+(B1.4)+(C2.1), (A1.1)+(B1.5)+(C2.1), (A1.1)+(B1.6)+(C2.1), (A1.1)+(B1.7)+(C2.1), (A1.1)+(B1.8)+(C2.1), (A1.1)+(B2.1)+(C2.1), (A1.1)+(B2.2)+(C2.1), (A1.1)+(B2.3)+(C2.1), (A1.1)+(B2.4)+(C2.1), (A1.1)+(B3.1)+(C2.1), (A1.1)+(B3.2)+(C2.1), (A1.1)+(B3.3)+(C2.1), (A1.1)+(B4.1)+(C2.1), (A1.1)+(B4.2)+(C2.1), (A1.1)+(B4.3)+(C2.1);
(A1.2)+(B1.1)+(C2.1), (A1.2)+(B1.2)+(C2.1), (A1.2)+(B1.3)+(C2.1), (A1.2)+(B1.4)+(C2.1), (A1.2)+(B1.5)+(C2.1), (A1.2)+(B1.6)+(C2.1), (A1.2)+(B1.7)+(C2.1), (A1.2)+(B1.8)+(C2.1), (A1.2)+(B2.1)+(C2.1), (A1.2)+(B2.2)+(C2.1), (A1.2)+(B2.3)+(C2.1), (A1.2)+(B2.4)+(C2.1), (A1.2)+(B3.1)+(C2.1), (A1.2)+(B3.2)+(C2.1), (A1.2)+(B3.3)+(C2.1), (A1.2)+(B4.1)+(C2.1), (A1.2)+(B4.2)+(C2.1), (A1.2)+(B4.3)+(C2.1);
(A1.1)+(B1.1)+(C2.2), (A1.1)+(B1.2)+(C2.2), (A1.1)+(B1.3)+(C2.2), (A1.1)+(B1.4)+(C2.2), (A1.1)+(B1.5)+(C2.2), (A1.1)+(B1.6)+(C2.2), (A1.1)+(B1.7)+(C2.2), (A1.1)+(B1.8)+(C2.2), (A1.1)+(B2.1)+(C2.2), (A1.1)+(B2.2)+(C2.2), (A1.1)+(B2.3)+(C2.2), (A1.1)+(B2.4)+(C2.2), (A1.1)+(B3.1)+(C2.2), (A1.1)+(B3.2)+(C2.2), (A1.1)+(B3.3)+(C2.2), (A1.1)+(B4.1)+(C2.2), (A1.1)+(B4.2)+(C2.2), (A1.1)+(B4.3)+(C2.2);
(A1.2)+(B1.1)+(C2.2), (A1.2)+(B1.2)+(C2.2), (A1.2)+(B1.3)+(C2.2), (A1.2)+(B1.4)+(C2.2), (A1.2)+(B1.5)+(C2.2), (A1.2)+(B1.6)+(C2.2), (A1.2)+(B1.7)+(C2.2), (A1.2)+(B1.8)+(C2.2), (A1.2)+(B2.1)+(C2.2), (A1.2)+(B2.2)+(C2.2), (A1.2)+(B2.3)+(C2.2), (A1.2)+(B2.4)+(C2.2), (A1.2)+(B3.1)+(C2.2), (A1.2)+(B3.2)+(C2.2), (A1.2)+(B3.3)+(C2.2), (A1.2)+(B4.1)+(C2.2), (A1.2)+(B4.2)+(C2.2), (A1.2)+(B4.3)+(C2.2);
(A1.1)+(B1.1)+(C2.3), (A1.1)+(B1.2)+(C2.3), (A1.1)+(B1.3)+(C2.3), (A1.1)+(B1.4)+(C2.3), (A1.1)+(B1.5)+(C2.3), (A1.1)+(B1.6)+(C2.3), (A1.1)+(B1.7)+(C2.3), (A1.1)+(B1.8)+(C2.3), (A1.1)+(B2.1)+(C2.3), (A1.1)+(B2.2)+(C2.3), (A1.1)+(B2.3)+(C2.3), (A1.1)+(B2.4)+(C2.3), (A1.1)+(B3.1)+(C2.3), (A1.1)+(B3.2)+(C2.3), (A1.1)+(B3.3)+(C2.3), (A1.1)+(B4.1)+(C2.3), (A1.1)+(B4.2)+(C2.3), (A1.1)+(B4.3)+(C2.3);
(A1.2)+(B1.1)+(C2.3), (A1.2)+(B1.2)+(C2.3), (A1.2)+(B1.3)+(C2.3), (A1.2)+(B1.4)+(C2.3), (A1.2)+(B1.5)+(C2.3), (A1.2)+(B1.6)+(C2.3), (A1.2)+(B1.7)+(C2.3), (A1.2)+(B1.8)+(C2.3), (A1.2)+(B2.1)+(C2.3), (A1.2)+(B2.2)+(C2.3), (A1.2)+(B2.3)+(C2.3), (A1.2)+(B2.4)+(C2.3), (A1.2)+(B3.1)+(C2.3), (A1.2)+(B3.2)+(C2.3), (A1.2)+(B3.3)+(C2.3), (A1.2)+(B4.1)+(C2.3), (A1.2)+(B4.2)+(C2.3), (A1.2)+(B4.3)+(C2.3);
(A1.1)+(B1.1)+(C2.4), (A1.1)+(B1.2)+(C2.4), (A1.1)+(B1.3)+(C2.4), (A1.1)+(B1.4)+(C2.4), (A1.1)+(B1.5)+(C2.4), (A1.1)+(B1.6)+(C2.4), (A1.1)+(B1.7)+(C2.4), (A1.1)+(B1.8)+(C2.4), (A1.1)+(B2.1)+(C2.4), (A1.1)+(B2.2)+(C2.4), (A1.1)+(B2.3)+(C2.4), (A1.1)+(B2.4)+(C2.4), (A1.1)+(B3.1)+(C2.4), (A1.1)+(B3.2)+(C2.4), (A1.1)+(B3.3)+(C2.4), (A1.1)+(B4.1)+(C2.4), (A1.1)+(B4.2)+(C2.4), (A1.1)+(B4.3)+(C2.4);
(A1.2)+(B1.1)+(C2.4), (A1.2)+(B1.2)+(C2.4), (A1.2)+(B1.3)+(C2.4), (A1.2)+(B1.4)+(C2.4), (A1.2)+(B1.5)+(C2.4), (A1.2)+(B1.6)+(C2.4), (A1.2)+(B1.7)+(C2.4), (A1.2)+(B1.8)+(C2.4), (A1.2)+(B2.1)+(C2.4), (A1.2)+(B2.2)+(C2.4), (A1.2)+(B2.3)+(C2.4), (A1.2)+(B2.4)+(C2.4), (A1.2)+(B3.1)+(C2.4), (A1.2)+(B3.2)+(C2.4), (A1.2)+(B3.3)+(C2.4), (A1.2)+(B4.1)+(C2.4), (A1.2)+(B4.2)+(C2.4), (A1.2)+(B4.3)+(C2.4);
(A1.1)+(B1.1)+(C3.1), (A1.1)+(B1.2)+(C3.1), (A1.1)+(B1.3)+(C3.1), (A1.1)+(B1.4)+(C3.1), (A1.1)+(B1.5)+(C3.1), (A1.1)+(B1.6)+(C3.1), (A1.1)+(B1.7)+(C3.1), (A1.1)+(B1.8)+(C3.1), (A1.1)+(B2.1)+(C3.1), (A1.1)+(B2.2)+(C3.1), (A1.1)+(B2.3)+(C3.1), (A1.1)+(B2.4)+(C3.1), (A1.1)+(B3.1)+(C3.1), (A1.1)+(B3.2)+(C3.1), (A1.1)+(B3.3)+(C3.1), (A1.1)+(B4.1)+(C3.1), (A1.1)+(B4.2)+(C3.1), (A1.1)+(B4.3)+(C3.1);
(A1.2)+(B1.1)+(C3.1), (A1.2)+(B1.2)+(C3.1), (A1.2)+(B1.3)+(C3.1), (A1.2)+(B1.4)+(C3.1), (A1.2)+(B1.5)+(C3.1), (A1.2)+(B1.6)+(C3.1), (A1.2)+(B1.7)+(C3.1), (A1.2)+(B1.8)+(C3.1), (A1.2)+(B2.1)+(C3.1), (A1.2)+(B2.2)+(C3.1), (A1.2)+(B2.3)+(C3.1), (A1.2)+(B2.4)+(C3.1), (A1.2)+(B3.1)+(C3.1), (A1.2)+(B3.2)+(C3.1), (A1.2)+(B3.3)+(C3.1), (A1.2)+(B4.1)+(C3.1), (A1.2)+(B4.2)+(C3.1), (A1.2)+(B4.3)+(C3.1);
(A1.1)+(B1.1)+(C3.2), (A1.1)+(B1.2)+(C3.2), (A1.1)+(B1.3)+(C3.2), (A1.1)+(B1.4)+(C3.2), (A1.1)+(B1.5)+(C3.2), (A1.1)+(B1.6)+(C3.2), (A1.1)+(B1.7)+(C3.2), (A1.1)+(B1.8)+(C3.2), (A1.1)+(B2.1)+(C3.2), (A1.1)+(B2.2)+(C3.2), (A1.1)+(B2.3)+(C3.2), (A1.1)+(B2.4)+(C3.2), (A1.1)+(B3.1)+(C3.2), (A1.1)+(B3.2)+(C3.2), (A1.1)+(B3.3)+(C3.2), (A1.1)+(B4.1)+(C3.2), (A1.1)+(B4.2)+(C3.2), (A1.1)+(B4.3)+(C3.2);
(A1.2)+(B1.1)+(C3.2), (A1.2)+(B1.2)+(C3.2), (A1.2)+(B1.3)+(C3.2), (A1.2)+(B1.4)+(C3.2), (A1.2)+(B1.5)+(C3.2), (A1.2)+(B1.6)+(C3.2), (A1.2)+(B1.7)+(C3.2), (A1.2)+(B1.8)+(C3.2), (A1.2)+(B2.1)+(C3.2), (A1.2)+(B2.2)+(C3.2), (A1.2)+(B2.3)+(C3.2), (A1.2)+(B2.4)+(C3.2), (A1.2)+(B3.1)+(C3.2), (A1.2)+(B3.2)+(C3.2), (A1.2)+(B3.3)+(C3.2), (A1.2)+(B4.1)+(C3.2), (A1.2)+(B4.2)+(C3.2), (A1.2)+(B4.3)+(C3.2);
(A1.1)+(B1.1)+(C4), (A1.1)+(B1.2)+(C4), (A1.1)+(B1.3)+(C4), (A1.1)+(B1.4)+(C4), (A1.1)+(B1.5)+(C4), (A1.1)+(B1.6)+(C4), (A1.1)+(B1.7)+(C4), (A1.1)+(B1.8)+(C4), (A1.1)+(B2.1)+(C4), (A1.1)+(B2.2)+(C4), (A1.1)+(B2.3)+(C4), (A1.1)+(B2.4)+(C4), (A1.1)+(B3.1)+(C4), (A1.1)+(B3.2)+(C4), (A1.1)+(B3.3)+(C4), (A1.1)+(B4.1)+(C4), (A1.1)+(B4.2)+(C4), (A1.1)+(B4.3)+(C4);
(A1.2)+(B1.1)+(C4), (A1.2)+(B1.2)+(C4), (A1.2)+(B1.3)+(C4), (A1.2)+(B1.4)+(C4), (A1.2)+(B1.5)+(C4), (A1.2)+(B1.6)+(C4), (A1.2)+(B1.7)+(C4), (A1.2)+(B1.8)+(C4), (A1.2)+(B2.1)+(C4), (A1.2)+(B2.2)+(C4), (A1.2)+(B2.3)+(C4), (A1.2)+(B2.4)+(C4), (A1.2)+(B3.1)+(C4), (A1.2)+(B3.2)+(C4), (A1.2)+(B3.3)+(C4), (A1.2)+(B4.1)+(C4), (A1.2)+(B4.2)+(C4), (A1.2)+(B4.3)+(C4);
(A1.1)+(B1.1)+(C5.1), (A1.1)+(B1.2)+(C5.1), (A1.1)+(B1.3)+(C5.1), (A1.1)+(B1.4)+(C5.1), (A1.1)+(B1.5)+(C5.1), (A1.1)+(B1.6)+(C5.1), (A1.1)+(B1.7)+(C5.1), (A1.1)+(B1.8)+(C5.1), (A1.1)+(B2.1)+(C5.1), (A1.1)+(B2.2)+(C5.1), (A1.1)+(B2.3)+(C5.1), (A1.1)+(B2.4)+(C5.1), (A1.1)+(B3.1)+(C5.1), (A1.1)+(B3.2)+(C5.1), (A1.1)+(B3.3)+(C5.1), (A1.1)+(B4.1)+(C5.1), (A1.1)+(B4.2)+(C5.1), (A1.1)+(B4.3)+(C5.1);
(A1.2)+(B1.1)+(C5.1), (A1.2)+(B1.2)+(C5.1), (A1.2)+(B1.3)+(C5.1), (A1.2)+(B1.4)+(C5.1), (A1.2)+(B1.5)+(C5.1), (A1.2)+(B1.6)+(C5.1), (A1.2)+(B1.7)+(C5.1), (A1.2)+(B1.8)+(C5.1), (A1.2)+(B2.1)+(C5.1), (A1.2)+(B2.2)+(C5.1), (A1.2)+(B2.3)+(C5.1), (A1.2)+(B2.4)+(C5.1), (A1.2)+(B3.1)+(C5.1), (A1.2)+(B3.2)+(C5.1), (A1.2)+(B3.3)+(C5.1), (A1.2)+(B4.1)+(C5.1), (A1.2)+(B4.2)+(C5.1), (A1.2)+(B4.3)+(C5.1);

(A1.1)+(B1.1)+(C6), (A1.1)+(B1.2)+(C6), (A1.1)+(B1.3)+(C6), (A1.1)+(B1.4)+(C6), (A1.1)+(B1.5)+(C6), (A1.1)+(B1.6)+(C6), (A1.1)+(B1.7)+(C6), (A1.1)+(B1.8)+(C6), (A1.1)+(B2.1)+(C6), (A1.1)+(B2.2)+(C6), (A1.1)+(B2.3)+(C6), (A1.1)+(B2.4)+(C6), (A1.1)+(B3.1)+(C6), (A1.1)+(B3.2)+(C6), (A1.1)+(B3.3)+(C6), (A1.1)+(B4.1)+(C6), (A1.1)+(B4.2)+(C6), (A1.1)+(B4.3)+(C6);

(A1.2)+(B1.1)+(C6), (A1.2)+(B1.2)+(C6), (A1.2)+(B1.3)+(C6), (A1.2)+(B1.4)+(C6), (A1.2)+(B1.5)+(C6), (A1.2)+(B1.6)+(C6), (A1.2)+(B1.7)+(C6), (A1.2)+(B1.8)+(C6), (A1.2)+(B2.1)+(C6), (A1.2)+(B2.2)+(C6), (A1.2)+(B2.3)+(C6), (A1.2)+(B2.4)+(C6), (A1.2)+(B3.1)+(C6), (A1.2)+(B3.2)+(C6), (A1.2)+(B3.3)+(C6), (A1.2)+(B4.1)+(C6), (A1.2)+(B4.2)+(C6), (A1.2)+(B4.3)+(C6);

(A1.1)+(B1.1)+(C7), (A1.1)+(B1.2)+(C7), (A1.1)+(B1.3)+(C7), (A1.1)+(B1.4)+(C7), (A1.1)+(B1.5)+(C7), (A1.1)+(B1.6)+(C7), (A1.1)+(B1.7)+(C7), (A1.1)+(B1.8)+(C7), (A1.1)+(B2.1)+(C7), (A1.1)+(B2.2)+(C7), (A1.1)+(B2.3)+(C7), (A1.1)+(B2.4)+(C7), (A1.1)+(B3.1)+(C7), (A1.1)+(B3.2)+(C7), (A1.1)+(B3.3)+(C7), (A1.1)+(B4.1)+(C7), (A1.1)+(B4.2)+(C7), (A1.1)+(B4.3)+(C7);

(A1.2)+(B1.1)+(C7), (A1.2)+(B1.2)+(C7), (A1.2)+(B1.3)+(C7), (A1.2)+(B1.4)+(C7), (A1.2)+(B1.5)+(C7), (A1.2)+(B1.6)+(C7), (A1.2)+(B1.7)+(C7), (A1.2)+(B1.8)+(C7), (A1.2)+(B2.1)+(C7), (A1.2)+(B2.2)+(C7), (A1.2)+(B2.3)+(C7), (A1.2)+(B2.4)+(C7), (A1.2)+(B3.1)+(C7), (A1.2)+(B3.2)+(C7), (A1.2)+(B3.3)+(C7), (A1.2)+(B4.1)+(C7), (A1.2)+(B4.2)+(C7), (A1.2)+(B4.3)+(C7);

(A1.1)+(B1.1)+(C8.1), (A1.1)+(B1.2)+(C8.1), (A1.1)+(B1.3)+(C8.1), (A1.1)+(B1.4)+(C8.1), (A1.1)+(B1.5)+(C8.1), (A1.1)+(B1.6)+(C8.1), (A1.1)+(B1.7)+(C8.1), (A1.1)+(B1.8)+(C8.1), (A1.1)+(B2.1)+(C8.1), (A1.1)+(B2.2)+(C8.1), (A1.1)+(B2.3)+(C8.1), (A1.1)+(B2.4)+(C8.1), (A1.1)+(B3.1)+(C8.1), (A1.1)+(B3.2)+(C8.1), (A1.1)+(B3.3)+(C8.1), (A1.1)+(B4.1)+(C8.1), (A1.1)+(B4.2)+(C8.1), (A1.1)+(B4.3)+(C8.1);

(A1.2)+(B1.1)+(C8.1), (A1.2)+(B1.2)+(C8.1), (A1.2)+(B1.3)+(C8.1), (A1.2)+(B1.4)+(C8.1), (A1.2)+(B1.5)+(C8.1), (A1.2)+(B1.6)+(C8.1), (A1.2)+(B1.7)+(C8.1), (A1.2)+(B1.8)+(C8.1), (A1.2)+(B2.1)+(C8.1), (A1.2)+(B2.2)+(C8.1), (A1.2)+(B2.3)+(C8.1), (A1.2)+(B2.4)+(C8.1), (A1.2)+(B3.1)+(C8.1), (A1.2)+(B3.2)+(C8.1), (A1.2)+(B3.3)+(C8.1), (A1.2)+(B4.1)+(C8.1), (A1.2)+(B4.2)+(C8.1), (A1.2)+(B4.3)+(C8.1).

Here the application rate ranges and application rate ratios mentioned above are in each case preferred. In addition, each of the 2-component and 3-component combinations mentioned above may also comprise one or more safeners, in particular a safener such as mefenpyr-diethyl (S1-1), isoxadifen-ethyl (S1-9), cloquintocet-mexyl (S2-1) and cyprosulfamide (S3-1), for example:

(A1.1)+(B1.1)+(S1-1), (A1.1)+(B1.2)+(S1-1), (A1.1)+(B1.3)+(S1-1), (A1.1)+(B1.4)+(S1-1), (A1.1)+(B1.5)+(S1-1), (A1.1)+(B1.6)+(S1-1), (A1.1)+(B1.7)+(S1-1), (A1.1)+(B1.8)+(S1-1), (A1.1)+(B2.1)+(S1-1), (A1.1)+(B2.2)+(S1-1), (A1.1)+(B2.3)+(S1-1), (A1.1)+(B2.4)+(S1-1), (A1.1)+(B3.1)+(S1-1), (A1.1)+(B3.2)+(S1-1), (A1.1)+(B3.3)+(S1-1), (A1.1)+(B4.1)+(S1-1), (A1.1)+(B4.2)+(S1-1), (A1.1)+(B4.3)+(S1-1);

(A1.1)+(B1.1)+(S1-9), (A1.1)+(B1.2)+(S1-9), (A1.1)+(B1.3)+(S1-9), (A1.1)+(B1.4)+(S1-9), (A1.1)+(B1.5)+(S1-9), (A1.1)+(B1.6)+(S1-9), (A1.1)+(B1.7)+(S1-9), (A1.1)+(B1.8)+(S1-9), (A1.1)+(B2.1)+(S1-9), (A1.1)+(B2.2)+(S1-9), (A1.1)+(B2.3)+(S1-9), (A1.1)+(B2.4)+(S1-9), (A1.1)+(B3.1)+(S1-9), (A1.1)+(B3.2)+(S1-9), (A1.1)+(B3.3)+(S1-9), (A1.1)+(B4.1)+(S1-9), (A1.1)+(B4.2)+(S1-9), (A1.1)+(B4.3)+(S1-9);

(A1.1)+(B1.1)+(S2-1), (A1.1)+(B1.2)+(S2-1), (A1.1)+(B1.3)+(S2-1), (A1.1)+(B1.4)+(S2-1), (A1.1)+(B1.5)+(S2-1), (A1.1)+(B1.6)+(S2-1), (A1.1)+(B1.7)+(S2-1), (A1.1)+(B1.8)+(S2-1), (A1.1)+(B2.1)+(S2-1), (A1.1)+(B2.2)+(S2-1), (A1.1)+(B2.3)+(S2-1), (A1.1)+(B2.4)+(S2-1), (A1.1)+(B3.1)+(S2-1), (A1.1)+(B3.2)+(S2-1), (A1.1)+(B3.3)+(S2-1), (A1.1)+(B4.1)+(S2-1), (A1.1)+(B4.2)+(S2-1), (A1.1)+(B4.3)+(S2-1);

(A1.1)+(B1.1)+(S3-1), (A1.1)+(B1.2)+(S3-1), (A1.1)+(B1.3)+(S3-1), (A1.1)+(B1.4)+(S3-1), (A1.1)+(B1.5)+(S3-1), (A1.1)+(B1.6)+(S3-1), (A1.1)+(B1.7)+(S3-1), (A1.1)+(B1.8)+(S3-1), (A1.1)+(B2.1)+(S3-1), (A1.1)+(B2.2)+(S3-1), (A1.1)+(B2.3)+(S3-1), (A1.1)+(B2.4)+(S3-1), (A1.1)+(B3.1)+(S3-1), (A1.1)+(B3.2)+(S3-1), (A1.1)+(B3.3)+(S3-1), (A1.1)+(B4.1)+(S3-1), (A1.1)+(B4.2)+(S3-1), (A1.1)+(B4.3)+(S3-1);

(A1.2)+(B1.1)+(S1-1), (A1.2)+(B1.2)+(S1-1), (A1.2)+(B1.3)+(S1-1), (A1.2)+(B1.4)+(S1-1), (A1.2)+(B1.5)+(S1-1), (A1.2)+(B1.6)+(S1-1), (A1.2)+(B1.7)+(S1-1), (A1.2)+(B1.8)+(S1-1), (A1.2)+(B2.1)+(S1-1), (A1.2)+(B2.2)+(S1-1), (A1.2)+(B2.3)+(S1-1), (A1.2)+(B2.4)+(S1-1), (A1.2)+(B3.1)+(S1-1), (A1.2)+(B3.2)+(S1-1), (A1.2)+(B3.3)+(S1-1), (A1.2)+(B4.1)+(S1-1), (A1.2)+(B4.2)+(S1-1), (A1.2)+(B4.3)+(S1-1);

(A1.2)+(B1.1)+(S1-9), (A1.2)+(B1.2)+(S1-9), (A1.2)+(B1.3)+(S-9), (A1.2)+(B1.4)+(S1-9), (A1.2)+(B1.5)+(S1-9), (A1.2)+(B1.6)+(S-9), (A1.2)+(B1.7)+(S1-9), (A1.2)+(B1.8)+(S1-9), (A1.2)+(B2.1)+(S1-9), (A1.2)+(B2.2)+(S1-9), (A1.2)+(B2.3)+(S1-9), (A1.2)+(B2.4)+(S1-9), (A1.2)+(B3.1)+(S1-9), (A1.2)+(B3.2)+(S1-9), (A1.2)+(B3.3)+(S1-9), (A1.2)+(B4.1)+(S1-9), (A1.2)+(B4.2)+(S1-9), (A1.2)+(B4.3)+(S1-9);

(A1.2)+(B1.1)+(S2-1), (A1.2)+(B1.2)+(S2-1), (A1.2)+(B1.3)+(S2-1), (A1.2)+(B1.4)+(S2-1), (A1.2)+(B1.5)+(S2-1), (A1.2)+(B1.6)+(S2-1), (A1.2)+(B1.7)+(S2-1), (A1.2)+(B1.8)+(S2-1), (A1.2)+(B2.1)+(S2-1), (A1.2)+(B2.2)+(S2-1), (A1.2)+(B2.3)+(S2-1), (A1.2)+(B2.4)+(S2-1), (A1.2)+(B3.1)+(S2-1), (A1.2)+(B3.2)+(S2-1), (A1.2)+(B3.3)+(S2-1), (A1.2)+(B4.1)+(S2-1), (A1.2)+(B4.2)+(S2-1), (A1.2)+(B4.3)+(S2-1);

(A1.2)+(B1.1)+(S3-1), (A1.2)+(B1.2)+(S3-1), (A1.2)+(B1.3)+(S3-1), (A1.2)+(B1.4)+(S3-1), (A1.2)+(B1.5)+(S3-1), (A1.2)+(B1.6)+(S3-1), (A1.2)+(B1.7)+(S3-1), (A1.2)+(B1.8)+(S3-1), (A1.2)+(B2.1)+(S3-1), (A1.2)+(B2.2)+(S3-1), (A1.2)+(B2.3)+(S3-1), (A1.2)+(B2.4)+(S3-1), (A1.2)+(B3.1)+(S3-1), (A1.2)+(B3.2)+(S3-1), (A1.2)+(B3.3)+(S3-1), (A1.2)+(B4.1)+(S3-1), (A1.2)+(B4.2)+(S3-1), (A1.2)+(B4.3)+(S3-1);

(A1.1)+(B1.1)+(S1-1)+(C1.1), (A1.1)+(B1.2)+(S1-1)+(C1.1), (A1.1)+(B1.3)+(S1-1)+(C1.1), (A1.1)+(B1.4)+(S1-1)+(C1.1), (A1.1)+(B1.5)+(S1-1)+(C1.1), (A1.1)+(B1.6)+(S1-1)+(C1.1), (A1.1)+(B1.7)+(S1-1)+(C1.1), (A1.1)+(B1.8)+(S1-1)+(C1.1), (A1.1)+(B2.1)+(S1-1)+(C1.1), (A1.1)+(B2.2)+(S1-1)+(C1.1), (A1.1)+(B2.3)+(S1-1)+(C1.1), (A1.1)+(B2.4)+(S1-1)+(C1.1), (A1.1)+(B3.1)+(S1-1)+(C1.1), (A1.1)+(B3.2)+(S1-1)+(C1.1), (A1.1)+(B3.3)+(S1-1)+(C1.1), (A1.1)+(B4.1)+(S1-1)+(C1.1), (A1.1)+(B4.2)+(S1-1)+(C1.1), (A1.1)+(B4.3)+(S1-1)+(C1.1);

(A1.1)+(B1.1)+(S1-9)+(C1.1), (A1.1)+(B1.2)+(S1-9)+(C1.1), (A1.1)+(B1.3)+(S1-9)+(C1.1), (A1.1)+(B1.4)+(S1-9)+(C1.1), (A1.1)+(B1.5)+(S1-9)+(C1.1), (A1.1)+

(B1.6)+(S1-9)+(C1.1), (A1.1)+(B1.7)+(S1-9)+(C1.1), (A1.1)+(B1.8)+(S1-9)+(C1.1), (A1.1)+(B2.1)+(S1-9)+(C1.1), (A1.1)+(B2.2)+(S1-9)+(C1.1), (A1.1)+(B2.3)+(S1-9)+(C1.1), (A1.1)+(B2.4)+(S1-9)+(C1.1), (A1.1)+(B3.1)+(S1-9)+(C1.1), (A1.1)+(B3.2)+(S1-9)+(C1.1), (A1.1)+(B3.3)+(S1-9)+(C1.1), (A1.1)+(B4.1)+(S1-9)+(C1.1), (A1.1)+(B4.2)+(S1-9)+(C1.1), (A1.1)+(B4.3)+(S1-9)+(C1.1);

(A1.1)+(B1.1)+(S2-1)+(C1.1), (A1.1)+(B1.2)+(S2-1)+(C1.1), (A1.1)+(B1.3)+(S2-1)+(C1.1), (A1.1)+(B1.4)+(S2-1)+(C1.1), (A1.1)+(B1.5)+(S2-1)+(C1.1), (A1.1)+(B1.6)+(S2-1)+(C1.1), (A1.1)+(B1.7)+(S2-1)+(C1.1), (A1.1)+(B1.8)+(S2-1)+(C1.1), (A1.1)+(B2.1)+(S2-1)+(C1.1), (A1.1)+(B2.2)+(S2-1)+(C1.1), (A1.1)+(B2.3)+(S2-1)+(C1.1), (A1.1)+(B2.4)+(S2-1)+(C1.1), (A1.1)+(B3.1)+(S2-1)+(C1.1), (A1.1)+(B3.2)+(S2-1)+(C1.1), (A1.1)+(B3.3)+(S2-1)+(C1.1), (A1.1)+(B4.1)+(S2-1)+(C1.1), (A1.1)+(B4.2)+(S2-1)+(C1.1), (A1.1)+(B4.3)+(S2-1)+(C1.1);

(A1.1)+(B1.1)+(S3-1)+(C1.1), (A1.1)+(B1.2)+(S3-1)+(C1.1), (A1.1)+(B1.3)+(S3-1)+(C1.1), (A1.1)+(B1.4)+(S3-1)+(C1.1), (A1.1)+(B1.5)+(S3-1)+(C1.1), (A1.1)+(B1.6)+(S3-1)+(C1.1), (A1.1)+(B1.7)+(S3-1)+(C1.1), (A1.1)+(B1.8)+(S3-1)+(C1.1), (A1.1)+(B2.1)+(S3-1)+(C1.1), (A1.1)+(B2.2)+(S3-1)+(C1.1), (A1.1)+(B2.3)+(S3-1)+(C1.1), (A1.1)+(B2.4)+(S3-1)+(C1.1), (A1.1)+(B3.1)+(S3-1)+(C1.1), (A1.1)+(B3.2)+(S3-1)+(C1.1), (A1.1)+(B3.3)+(S3-1)+(C1.1), (A1.1)+(B4.1)+(S3-1)+(C1.1), (A1.1)+(B4.2)+(S3-1)+(C1.1), (A1.1)+(B4.3)+(S3-1)+(C1.1);

(A1.2)+(B1.1)+(S1-1)+(C1.1), (A1.2)+(B1.2)+(S1-1)+(C1.1), (A1.2)+(B1.3)+(S1-1)+(C1.1), (A1.2)+(B1.4)+(S1-1)+(C1.1), (A1.2)+(B1.5)+(S1-1)+(C1.1), (A1.2)+(B1.6)+(S1-1)+(C1.1), (A1.2)+(B1.7)+(S1-1)+(C1.1), (A1.2)+(B1.8)+(S1-1)+(C1.1), (A1.2)+(B2.1)+(S1-1)+(C1.1), (A1.2)+(B2.2)+(S1-1)+(C1.1), (A1.2)+(B2.3)+(S1-1)+(C1.1), (A1.2)+(B2.4)+(S1-1)+(C1.1), (A1.2)+(B3.1)+(S1-1)+(C1.1), (A1.2)+(B3.2)+(S1-1)+(C1.1), (A1.2)+(B3.3)+(S1-1)+(C1.1), (A1.2)+(B4.1)+(S1-1)+(C1.1), (A1.2)+(B4.2)+(S1-1)+(C1.1), (A1.2)+(B4.3)+(S1-1)+(C1.1);

(A1.2)+(B1.1)+(S1-9)+(C1.1), (A1.2)+(B1.2)+(S1-9)+(C1.1), (A1.2)+(B1.3)+(S1-9)+(C1.1), (A1.2)+(B1.4)+(S1-9)+(C1.1), (A1.2)+(B1.5)+(S1-9)+(C1.1), (A1.2)+(B1.6)+(S1-9)+(C1.1), (A1.2)+(B1.7)+(S1-9)+(C1.1), (A1.2)+(B1.8)+(S1-9)+(C1.1), (A1.2)+(B2.1)+(S1-9)+(C1.1), (A1.2)+(B2.2)+(S1-9)+(C1.1), (A1.2)+(B2.3)+(S1-9)+(C1.1), (A1.2)+(B2.4)+(S1-9)+(C1.1), (A1.2)+(B3.1)+(S1-9)+(C1.1), (A1.2)+(B3.2)+(S1-9)+(C1.1), (A1.2)+(B3.3)+(S1-9)+(C1.1), (A1.2)+(B4.1)+(S1-9)+(C1.1), (A1.2)+(B4.2)+(S1-9)+(C1.1), (A1.2)+(B4.3)+(S1-9)+(C1.1);

(A1.2)+(B1.1)+(S2-1)+(C1.1), (A1.2)+(B1.2)+(S2-1)+(C1.1), (A1.2)+(B1.3)+(S2-1)+(C1.1), (A1.2)+(B1.4)+(S2-1)+(C1.1), (A1.2)+(B1.5)+(S2-1)+(C1.1), (A1.2)+(B1.6)+(S2-1)+(C1.1), (A1.2)+(B1.7)+(S2-1)+(C1.1), (A1.2)+(B1.8)+(S2-1)+(C1.1), (A1.2)+(B2.1)+(S2-1)+(C1.1), (A1.2)+(B2.2)+(S2-1)+(C1.1), (A1.2)+(B2.3)+(S2-1)+(C1.1), (A1.2)+(B2.4)+(S2-1)+(C1.1), (A1.2)+(B3.1)+(S2-1)+(C1.1), (A1.2)+(B3.2)+(S2-1)+(C1.1), (A1.2)+(B3.3)+(S2-1)+(C1.1), (A1.2)+(B4.1)+(S2-1)+(C1.1), (A1.2)+(B4.2)+(S2-1)+(C1.1), (A1.2)+(B4.3)+(S2-1)+(C1.1);

(A1.2)+(B1.1)+(S3-1)+(C1.1), (A1.2)+(B1.2)+(S3-1)+(C1.1), (A1.2)+(B1.3)+(S3-1)+(C1.1), (A1.2)+(B1.4)+(S3-1)+(C1.1), (A1.2)+(B1.5)+(S3-1)+(C1.1), (A1.2)+(B1.6)+(S3-1)+(C1.1), (A1.2)+(B1.7)+(S3-1)+(C1.1), (A1.2)+(B1.8)+(S3-1)+(C1.1), (A1.2)+(B2.1)+(S3-1)+(C1.1), (A1.2)+(B2.2)+(S3-1)+(C1.1), (A1.2)+(B2.3)+(S3-1)+(C1.1), (A1.2)+(B2.4)+(S3-1)+(C1.1), (A1.2)+(B3.1)+(S3-1)+(C1.1), (A1.2)+(B3.2)+(S3-1)+(C1.1), (A1.2)+(B3.3)+(S3-1)+(C1.1), (A1.2)+(B4.1)+(S3-1)+(C1.1), (A1.2)+(B4.2)+(S3-1)+(C1.1), (A1.2)+(B4.3)+(S3-1)+(C1.1).

The herbicide combinations according to the invention (=herbicidal compositions) have an outstanding herbicidal activity against a broad spectrum of economically important harmful plants. Here, the substances can be applied by the pre-sowing, the pre-emergence and/or the post-emergence method, for example jointly or separately. Post-emergence application, or early pre-emergence application, is preferred.

Specifically, examples may be mentioned of some representatives of the dicotyledonous weed flora which can be controlled by the combinations according to the invention, without the enumeration being a restriction to certain species: *Abutilon* spp., *Amaranthus* spp., *Chenopodium* spp., *Chrysanthemum* spp., *Galium* spp. such as *Galium aparine*, *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp. from among the annual weeds and *Convolvulus*, *Cirsium*, *Rumex* and *Artemisia* from among the perennial weeds, and also *Acacia* spp., *Acalypha acalopecurus*, *Ageratum conyzoides*, *Ammis majus*, *Apium leptophyllium*, *Asclepias curassayica*, *Baccharis coridifolia*, *Bauhinia* spp., *Baltimora recta*, *Boehmeria niveam*, *Bowlesia incana*, *Cassia occidentalis*, *Carduus acanthoides*, *Cassia tora*, *Chamaecrysta trichopoda*, *Cirsium vulgare*, *Cleome viscosa*, *Clidemia Hirta*, *Conyza bonariensis*, *Coronopus didimus*, *Crotalaria* spp., *Eclipta alba*, *Elephantopus spicatus*, *Eupatorium squalidum*, *Euphorbia* spp., *Fumaria capriolata*, *Fumaria officinalis*, *Gamochaeta spicata*, *Gnaphallium* spp., *Heliconia bijai*, *Hyptis suaveolens*, *Lantana camara*, *Lippia nudiflora*, *Ludwigia octovalvis*, *Malva* spp., *Melampodium* spp., *Mimosa* spp., *Mucuna pririens*, *Nephrolepsis* spp., *Pachira odorata*, *Petiveria alleacea*, *Phitecollobium* spp., *Pisonia aculeata*, *Plantago lanceolata*, *Plantago major*, *Priva lapulacea*, *Prosopis juliflora*, *Pteridium aquilinum*, *Rauvolfia tetraphilla*, *Ricinus comunis*, *Scleria pterota*, *Senecio brasiliensis*, *Senna obtusifolia*, *Silibum marianun*, *Tecoma stans*, *Thalia geniculata*, *Vernonia* spp., *Viguiera dentata*, *Wissadula amplissima*.

If the herbicide combinations according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth likewise stops drastically a very short time after the treatment and the weed plants remain at the growth stage of the point in time of application, or they die completely after a certain time, so that in this manner competition by the weeds, which is harmful to the crop plants, is eliminated at a very early point in time and in a sustained manner.

The herbicidal compositions according to the invention are distinguished by a rapidly commencing and long-lasting herbicidal action. As a rule, the rainfastness of the active compounds in the combinations according to the invention is advantageous. A particular advantage is that the dosages of the compounds (A) and (B), which are used in the combinations and are effective, can be adjusted to such a low quantity that their soil action is optimally low. Not only does this allow them to be employed in sensitive crops in the first place, but groundwater contaminations are virtually avoided. The herbicide combination according to the invention allows the application rate of the active compounds required to be reduced considerably.

In a preferred embodiment, when herbicides of the type (A)+(B) are used jointly, superadditive (=synergistic) effects are observed. This means that the effect in the combinations exceeds the expected total of the effects of the individual herbicides employed. The synergistic effects allow the application rate to be reduced, a broader spectrum of broad-leaved weeds and grass weeds to be controlled, the herbicidal action to take place more rapidly, the duration of action to be longer, the harmful plants to be controlled better while using only one, or few, applications, and the application period which is possible to be extended.

The abovementioned properties and advantages are of benefit for weed control practice to keep agricultural crops free from undesired competing plants and thus to safeguard and/or increase the yields from the qualitative and quantitative point of view. These novel combinations markedly exceed the technical state of the art with a view to the properties described.

While the combinations according to the invention have an outstanding herbicidal activity against harmful plants, the crop plants are damaged only to a minor extent, if at all.

Moreover, some of the combinations according to the invention have outstanding growth-regulatory properties on the crop plants. They engage in the plants' metabolism in a regulatory manner and can thus be employed for provoking directed effects on plant constituents and to facilitate harvesting such as for example by triggering desiccation and stunted growth. Moreover, they are also suitable for the general control and inhibition of undesired vegetative growth without simultaneously destroying the plants. An inhibition of vegetative growth is very important in a large number of monocotyledonous and dicotyledonous crops since yield losses as a result of lodging can thus be reduced, or prevented completely.

Owing to their herbicidal and plant-growth-regulatory properties, the combinations according to the invention can also be employed for controlling harmful plants in genetically modified crop plants or crop plants obtained by mutation/selection. These crop plants are distinguished as a rule by particular, advantageous properties, such as resistances to herbicidal compositions or resistances to plant diseases or causative agents of plant diseases such as particular insects or microorganisms such as fungi, bacteria or viruses. Other particular properties relate, for example, to the harvested material with regard to quantity, quality, storability, composition and specific constituents. Thus, for example, transgenic plants are known whose starch content is increased or whose starch quality is altered, or those where the harvested material has a different fatty acid composition.

Conventional methods of generating novel plants which have modified properties in comparison to plants occurring to date consist, for example, in traditional breeding methods and the generation of mutants (see, for example, U.S. Pat. No. 5,162,602; U.S. Pat. No. 4,761,373; U.S. Pat. No. 4,443,971). Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which exhibit resistances to other herbicides, for example to sulfonylureas (EP-A-0257993, U.S. Pat. No. 5,013,659), transgenic crop plants with the capability of producing Bacillus thuringiensis toxins (Bt toxins), which make the plants resistant to certain pests (EP-A-0142924, EP-A-0193259), transgenic crop plants with a modified fatty acid composition (WO 91/13972).

A large number of techniques in molecular biology are known in principle with the aid of which novel transgenic plants with modified properties can be generated: see, for example, Sambrook et al., 1989, Molecular Cloning, A Laboratory Manual, $2^{nd}$ Edition, Cold Spring Harbor Laboratory Press, Cold Spring Harbor, N.Y.; or Winnacker "Gene und Klone", VCH Weinheim $2^{nd}$ Edition 1996 or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, the abovementioned standard methods allow base exchanges to be carried out, subsequences to be removed, or natural or synthetic sequences to be added. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the encoding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give rise to intact plants. In principle, the transgenic plants can be plants of any desired plant species, i.e. not only monocotyledonous, but also dicotyledonous, plants. Thus, transgenic plants can be obtained whose properties are altered by overexpression, suppression or inhibition of homologous (=natural) genes or gene sequences or the expression of heterologous (=foreign) genes or gene sequences.

The present invention furthermore provides a method for controlling unwanted plant growth, preferably in plant crops such as monocotyledonous or dicotyledonous plant crops, for example pasture crops, cereals (for example wheat, barley, rye, oats, rice, corn and millet), sugar beet, sugar cane, oilseed rape, cotton and soybeans, preferably in monocotyledonous crops such as pasture crops or cereals (for example wheat, barley, rye, oats, rice, corn and millet), where one or more herbicides of type (A) and one or more herbicides of type (B) are applied jointly or separately to the harmful plants, plant parts, plant seeds or to the area on which the plants grow, for example the area under cultivation or the pasture area.

The herbicide combinations according to the invention are used with particular preference in pasture crops, in particular grass crops, such as native perennial grass species, *Brachiaria* (*brizantha, ruziziensis, decumbens*), *Panicum maximum, Cynodon plesctostachyum, Andropogum gayanus, Dichantium aristatum, Digitaria decumbens* (Pangola), *Panicum maximum, Medicago sativa* (Alfalfa), *Trifolium pratense, Trifolium repens, Melilotus officinalis, Lotus corniculatus, Lotus tenuis, Bromus unioloides, Colium* spp. une, *Lolium multiflorum* or *Lolium perenne, Festuca arundinacea, Dactylis glomerata, Phalaris bulbosa, Agropirum repens.*

The plant crops can also have been genetically modified or been obtained by mutation/selection and are preferably tolerant to acetolactate synthase (ALS) inhibitors.

The invention also relates to the use of the herbicide combinations according to the invention for controlling harmful plants, preferably in plant crops.

The herbicide combinations according to the invention can exist not only as mixed formulations of the components (A) and (B), if appropriate together with further agrochemically active compounds, additives and/or customary formulation auxiliaries, which are then applied in the customary manner, for example as a dilution with water, but also as so-called tank mixes by jointly diluting the separately formulated, or partially separately formulated, components with water.

The components (A) and (B) or their combinations can be formulated in various ways, depending on the prevailing biological and/or chemical-physical parameters. The following are examples of general possibilities for formulations: wettable powders (WP), water-soluble concentrates, emulsifiable concentrates (EC), aqueous solutions (SL), emulsions (EW) such as oil-in-water and water-in-oil emulsions, sprayable solutions or emulsions, suspension concentrates (SC), oil- or water-based dispersions, such as oil suspension concentrates (OD), suspoemulsions, dusts (DP), seed-dressing materials, granules for soil application or for broadcasting, or water-dispersible granules (WG), ULV formulations, microcapsules or waxes.

The individual formulation types are known in principle and are described for example in: Winnacker-Küchler, "Chemische Technologie", Volume 7, C. Hanser Verlag Munich, 4$^{th}$ Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required such as inert materials, surfactants, solvents and other additives are also known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Surface-active ethylene oxide adducts], Wiss. Verlagsgesellschaft, Stuttgart 1976, Winnacker-Küchler, "Chemische Technologie", Volume 7, C. Hanser Verlag Munich, 4$^{th}$ Edition 1986.

Based on these formulations, combinations with other agrochemically active compounds, such as other herbicides, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active compound, also comprise ionic or nonionic surfactants (wetting agents, dispersants), for example polyoxyethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltauride, in addition to a diluent or inert material.

Emulsifiable concentrates are prepared by dissolving the active compound in an organic solvent, for example butanol, cyclohexanone, dimethylformamide, xylene or else higher-boiling aromatics or hydrocarbons with addition of one or more ionic or nonionic surfactants (emulsifiers). Examples of emulsifiers which may be used are: calcium salts of alkylarylsulfonic acids, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained by grinding the active compound with finely divided solid materials, for example talc, natural clays such as kaolin, bentonite and pyrophyllite, or diatomaceous earth.

Suspension concentrates (SC) can be water- or oil-based. They can be prepared, for example, by wet grinding by means of commercially available bead mills and, if appropriate, addition of further surfactants as they have already been mentioned for example above in the case of the other formulation types.

Emulsions, for example oil-in-water emulsions (EW), can be prepared for example by means of stirrers, colloid mills and/or static mixers using aqueous organic solvents and, if appropriate, further surfactants as have already been mentioned for example above in the case of the other formulation types.

Granules can be prepared either by spraying the active compound onto adsorptive, granulated inert material or by applying active compound concentrates to the surface of carriers such as sand, kaolinites or granulated inert material with the aid of binders, for example polyvinyl alcohol, sodium polyacrylate or else mineral oils. Suitable active compounds may also be granulated in the manner conventionally used for the production of fertilizer granules, if desired in a mixture with fertilizers.

As a rule, water-dispersible granules are prepared by customary processes such as spray drying, fluidized-bed granulation, disk granulation, mixing with high-speed mixers and extrusion without solid inert material. Regarding the production of disk granules, fluidized-bed granules, extruder granules and spray granules, see, for example, methods in "Spray-Drying Handbook" 3rd ed. 1979, G. Goodwin Ltd., London; J. E. Browning, "Agglomeration", Chemical and Engineering 1967, page 147 et seq; "Perry's Chemical Engineer's Handbook", 5th Ed., McGraw-Hill, New York 1973, pp. 8-57.

The herbicide combinations according to the invention are preferably formulated in the form of an oil suspension concentrate (OD). The oil suspension concentrates comprise, for example, a) at least one of the herbicides (A) and (B), in suspended form, b) one or more organic solvents, c) optionally one or more sulfosuccinates, d) optionally one or more agrochemically active compounds different from a),
e) optionally one or more inorganic salts, and
f) optionally customary auxiliaries and additives.

The term oil suspension concentrate (OD) is to be understood as meaning a suspension concentrate based on organic solvents. Here, one or more active compounds are suspended in the organic solvent; further active compounds may be dissolved in the organic solvent.

In the oil suspension concentrates according to the invention, the herbicidally active compounds a) are generally present in amounts of from 0.01 to 50% by weight, preferably from 0.1 to 30% by weight; here and in the entire description, the term "% by weight" refers, unless defined otherwise, to the relative weight of the component in question, based on the total weight of the formulation. Preferred suspended herbicides a) are (A1.1) and (A1.2), the free acids and salts of (B1), (B2), (B3) and (B4), and also (C1), (C4), (C5), (C7), (C8) and the free acids of (C2) and (C3).

Suitable organic solvents (component b) are, for example:
1) hydrocarbons, which may be unsubstituted or substituted, for example
1a) aromatic hydrocarbons, for example
   mono- or polyalkyl-substituted benzenes, such as toluene, xylenes, mesitylene, ethylbenzene, or
   mono- or polyalkyl-substituted naphthalenes, such as 1-methylnaphthalene, 2-methylnaphthalene or dimethylnaphthalene, or
   other benzene-derived aromatic hydrocarbons, such as indane or Tetralin®, or
   mixtures thereof,
1b) aliphatic hydrocarbons, for example
   straight-chain or branched aliphatics, for example of the formula $C_nH_{2n+2}$, such as pentane, hexane, octane, 2-methylbutane or 2,2,4-trimethylpentane, or
   cyclic, optionally alkyl-substituted aliphatics, such as cyclohexane or methylcyclopentane, or
   mixtures thereof, such as solvents of the Exxsol® D series, Isopar® series or Bayol® series, for example Bayol® 82 (ExxonMobil Chemicals), or the Isane® IP series or Hydroseal® G series (TotalFinaElf),
1c) mixtures of aromatic and aliphatic hydrocarbons, such as solvents of the Solvesso® series, for example Solvesso® 100, Solvesso® 150 or Solvesso® 200 (ExxonMobil Chemicals), of the Solvarex®/Solvaro® series (TotalFinaElf) or the Caromax® series, for example Caromax® 28 (Petrochem Carless), or
1d) halogenated hydrocarbons, such as halogenated aromatic and aliphatic hydrocarbons, such as chlorobenzene or methylene chloride, or
2) polar solvents, for example aprotic polar solvents, such as fully etherified and fully esterified $C_1$-$C_9$-alkanoic acids which may be mono-, di- or polyfunctional, for example the ethers and esters with $C_1$-$C_{18}$-alkyl alcohols, ketones with a low tendency to tautomerize, phosphoric acid esters, amides, nitriles or sulfones, for example diisobutyl adipate, Rhodiasolv® RPDE (Rhodia), cyclohexanone, Jeffsol® PC (Huntsman), γ-butyrolactone, N-methylpyrrolidone, dimethyl sulfoxide, acetonitrile, tributylphosphatam or the Hostarex® PO series (Clariant), or protic polar solvents, such as alcohols, amines or carboxylic acids. The alcohols, amines or carboxylic acids preferably have 1 to 18 carbon atoms and can be straight-chain, branched or cyclic and saturated or unsaturated and may optionally comprise heteroatoms and be mono- or polyfunctional. Examples of alcohols are monohydric $C_1$-$C_{10}$-alcohols, such as methanol, ethanol, propanol, isopropanol, heptanol, octanol, isooctanol or phenol, or polyols, such as glycerol or polyglycols, commercially available, for example, as Exxal® series (ExxonMobil), Agrisynth® PA (ISP), Arcosolv® series (Lyondell Chemical) or Nacol® 6-98 (DEA). Examples of amines are diethylamine, hexylamine or aniline. Examples of carboxylic acids are adipic acid and adipic acid monoesters,
3) fatty acid esters, for example of natural origin, for example natural oils, such as animal oils or vegetable oils, or of synthetic origin, for example the Edenor® series, for example Edenor® MEPa or Edenor® MESU, or the Agnique® ME series or Agnique®AE series (Cognis), the Salim®ME series (Salim), the Radia® series, for example Radia® 30167 (ICI), the Prilube® series, for example Prilube® 1530 (Petrofina), the Stepan® C series (Stepan) or the Witconol® 23 series (Witco). The fatty acid esters are preferably esters of $C_{10}$-$C_{22}$-, with preference $C_{12}$-$C_{20}$-, fatty acids. The $C_{10}$-$C_{22}$-fatty acid esters are, for example, esters of unsaturated or saturated $C_{10}$-$C_{22}$-fatty acids, in particular those having an even number of carbon atoms, for example erucic acid, lauric acid, palmitic acid, and in particular $C_{18}$-fatty acids, such as stearic acid, oleic acid, linoleic acid or linolenic acid.
  Examples of fatty acid esters such as $C_{10}$-$C_{22}$-fatty acid esters are glycerol and glycol esters of fatty acids such as $C_{10}$-$C_{22}$-fatty acids, or transesterification products thereof, for example fatty acid alkyl esters such as $C_{10}$-$C_{22}$-fatty acid $C_1$-$C_{20}$-alkyl esters, which can be obtained, for example, by transesterification of the abovementioned glycerol or glycol fatty acid esters such as $C_{10}$-$C_{22}$-fatty acid esters with $C_1$-$C_{20}$-alcohols (for example methanol, ethanol, propanol or butanol). The transesterification can be carried out by known methods, as described, for example, in Römpp Chemie Lexikon, 9th edition, volume 2, page 1343, Thieme Verlag Stuttgart.
  Preferred fatty acid alkyl esters such as $C_{10}$-$C_{22}$-fatty acid $C_1$-$C_{20}$-alkyl esters are methyl esters, ethyl esters, propyl esters, butyl esters, 2-ethylhexyl esters and dodecyl esters. Preferred glycol and glycerol fatty acid esters such as $C_{10}$-$C_{22}$-fatty acid esters are the uniform or mixed glycol esters and glycerol esters of $C_{10}$-$C_{22}$-fatty acids, in particular of such fatty acids having an even number of carbon atoms, for example erucic acid, lauric acid, palmitic acid and in particular $C_{18}$-fatty acids such as stearic acid, oleic acid, linoleic acid or linolenic acid.

Animal oils b) are generally known and commercially available. For the purpose of the present invention, the term "animal oils" is to be understood as meaning, for example, oils of animal origin such as whale oil, cod-liver oil, musk oil or mink oil.

Vegetable oils b) are generally known and commercially available. For the purpose of the present invention, the term "vegetable oils" is to be understood as meaning, for example, oils of oleaginous plant species, such as soybean oil, rapeseed oil, corn oil, sunflower oil, cottonseed oil, linseed oil, coconut oil, palm oil, thistle oil, walnut oil, arachis oil, olive oil or castor oil, in particular rapeseed oil, where the vegetable oils also include their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-, fatty acids. The $C_{10}$-$C_{22}$-fatty acid esters are, for example, esters of unsaturated or saturated $C_{10}$-$C_{22}$-fatty acids having, in particular, an even number of carbon atoms, for example erucic acid, lauric acid, palmitic acid and in particular $C_{18}$-fatty acids such as stearic acid, oleic acid, linoleic acid or linolenic acid.

Examples of vegetable oils are $C_{10}$-$C_{22}$-fatty acid esters of glycerol or glycol with $C_{10}$-$C_{22}$-fatty acids, or $C_{10}$-$C_{22}$-fatty acid $C_1$-$C_{20}$-alkyl esters which can be obtained, for example, by transesterification of the glycerol or glycol $C_{10}$-$C_{22}$-fatty acid esters mentioned above with $C_1$-$C_{20}$-alcohols (for example methanol, ethanol, propanol or butanol). The transesterification can be carried out by known methods as described, for example, in Römpp Chemie Lexikon, 9th edition, volume 2, page 1343, Thieme Verlag Stuttgart.

The vegetable oils can be contained in the oil suspension concentrates according to the invention for example in the form of commercially available vegetable oils, in particular rapeseed oils, such as rapeseed oil methyl ester, for example Phytorob® B (Novance, France), Edenor® MESU and the Agnique® ME series (Cognis, Germany), the Radia® series (ICI), the Prilube® series (Petrofina), or biodiesel or in the form of commercially available plant-oil-containing formulation additives, in particular those based on rapeseed oils, such as rapeseed oil methyl esters, for example Hasten® (Victorian Chemical Company, Australia, hereinbelow referred to as Hasten, main ingredient: rapeseed oil ethyl ester), Actirob®B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

Examples of synthetic fatty acid esters are, for example, those derived from fatty acids having an odd number of carbon atoms, such as $C_{11}$-$C_{21}$-fatty acid esters.

Preferred organic solvents are aromatic hydrocarbons, aliphatic hydrocarbons and fatty acid esters, such as vegetable oils, such as triglycerides of fatty acids having 10 to 22 carbon atoms, which may be saturated or else unsaturated, straight-chain or branched and which may or may not carry further functional groups, such as corn oil, rapeseed oil, sunflower oil, cottonseed oil, linseed oil, soybean oil, coconut oil, palm oil, thistle oil or castor oil, and their transesterification products, such as fatty acid alkyl esters, and mixtures thereof.

The solvents may be present on their own or as a mixture. The total proportion of solvents in the oil suspension concentrates according to the invention is generally between 5 and 95% by weight, preferably in the range between 20 and 80% by weight. The proportion of polar solvents such as aprotic polar solvents is generally below 20% by weight, preferably in the range from 0 to 10% by weight.

The oil suspension concentrates according to the invention may optionally comprise sulfosuccinates (component c), for example mono- or diesters of sulfosuccinic acid, preferably those of the formula (III)

(III)

in which $R^1$ is H or an unsubstituted or substituted $C_1$-$C_{30}$-hydrocarbon radical, such as $C_1$-$C_{30}$-alkyl or $C_7$-$C_{30}$-alkylaryl, $R^2$ is H or an unsubstituted or substituted $C_1$-$C_{30}$-hydrocarbon radical, such as $C_1$-$C_{30}$-alkyl or $C_7$-$C_{30}$-alkylaryl, or a cation, for example a metal cation, such as an alkali metal or alkaline earth metal cation, or an ammonium cation, such as $NH_4$ or an alkyl-, alkylaryl- or poly(arylalkyl)-phenylammonium cation, $X^1$, $X^2$ are identical or different and independently of one another are a spacer unit, such as a polyether unit or a polyester unit, n, m are identical or different and independently of one another are zero or 1, preferably zero, and M is a cation, for example a metal cation, such as an alkali metal or alkaline earth metal cation, or an ammonium cation, such as $NH_4$ or an alkyl-, alkylaryl- or poly(arylalkyl)phenylammonium cation.

Preference is given to sulfosuccinates of the formula (III) in which $R^1$ and $R^2$ are identical or different and independently of one another are linear, branched or cyclic, saturated or unsaturated $C_1$-$C_{20}$-, preferably $C_4$-$C_{18}$-, alkyl radicals, such as methyl, ethyl, butyl, hexyl, cyclohexyl, octyl, such as 2-ethylhexyl, decyl, tridecyl or octadecyl radicals, or $R^1$ and $R^2$ are $C_7$-$C_{20}$-alkylaryl radicals, such as nonylphenyl, 2,4,6-tri-sec-butylphenyl, 2,4,6-tris(1-phenylethyl)phenyl, alkylbenzyl or a hydrocinnamic radical, $X_1$ and $X_2$ are identical or different and independently of one another are polyether units, such as polyethylene glycols —$(C_2H_4O)_p$— or polypropylene glycols —$(C_3H_6O)_p$— where p=1 to p=20, in particular p=1 to p=12, or polyester units, such as polyhydroxybutyric acid —$(CH[CH_3]$—$CH_2$—$COO)_q$— or polylactic acid —$(CH[CH_3]$—$COO)_q$— where q=1 to q=15, in particular q=1 to q=8, n, m are identical or different and independently of one another are zero or 1, preferably zero, and M is a cation, for example a metal cation, such as an alkali metal or alkaline earth metal cation, or an ammonium cation which may be alkyl-substituted.

Examples of sulfosuccinates present according to the invention are a1) sulfosuccinate which is esterified once or twice with linear, cyclic or branched aliphatic, cycloaliphatic and/or aromatic alcohols, having, for example, 1 to 22 carbon atoms in the alkyl radical, preferably mono- or dialkali metal sulfosuccinate, in particular mono- or disodium sulfosuccinate, which is esterified once or twice with methanol, ethanol, (iso)propanol, (iso)butanol, (iso)pentanol, (iso)hexanol, cyclohexanol, (iso)heptanol, (iso)octanol (in particular: ethylhexanol), (iso)nonanol, (iso)decanol, (iso)undecanol, (iso)dodecanol or (iso)tridecanol, a2) sulfosuccinate which is esterified once or twice with (poly)alkylene oxide adducts of alcohols, having, for example, 1 to 22 carbon atoms in the alkyl radical and 1 to 200, preferably 2 to 200, alkylene oxide units in the (poly)alkylene oxide moiety, preferably mono- or dialkali metal sulfosuccinate, in particular mono- or disodium sulfosuccinate, which is esterified once or twice with dodecyl/tetradecyl alcohol+2-5 mol of ethylene oxide or with i-tridecyl+3 mol of ethylene oxide, a3) the dialkali metal salt, preferably the disodium salt, of maleic anhydride which has been reacted with one equivalent of an amine or an amino-terminated (poly)alkylene oxide adduct of an alcohol, an amine, a fatty acid, an ester or an amide and then sulfonated, having, for example, 1 to 22 carbon atoms in the alkyl radical and 1 to 200, preferably 2 to 200, oxyalkylene units in the (poly)alkylene oxide moiety, preferably the disodium salt of maleic anhydride which has been reacted with one equivalent of coconut fatty amine and then sulfonated, a4) the dialkali metal salt, preferably the disodium salt, of maleic anhydride which has been reacted with one equivalent of an amide or a (poly)alkylene oxide adduct of an amide and then sulfonated, having, for example, 1 to 22 carbon atoms in the alkyl radical and 1 to 200, preferably 2 to 200, oxyalkylene units in the (poly)alkylene oxide moiety, preferably the disodium salt of maleic anhydride which has been reacted with one equivalent of oleylamide+2 mol of ethylene oxide and then sulfonated, and/or a5) the tetraalkali metal salt, preferably the tetrasodium salt, of N-(1,2-dicarboxy-ethyl)-N-octadecylsulfosuccinamate.

Examples of sulfosuccinates of groups a1) to a5) which are commercially available and preferred within the context of the present invention are listed below:

a1) sodium dialkylsulfosuccinate, for example sodium di($C_4$-$C_{18}$)alkylsulfosuccinate, such as sodium diisooctylsulfosuccinate, preferably sodium di(2-ethylhexyl)sulfosuccinate, commercially available, for example, in the form of the Aerosol® brands (Cytec), the Agrilan® or Lankropol® brands (Akzo Nobel), the Empimin® brands (Albright&Wilson), the Cropol® brands (Croda), the Lutensit® brands (BASF), the Triton® brands (Union Carbide), the Geropon® brands (Rhodia) or the Imbirol®, Madeol® or Polirol® brands (Cesalpinia), a2) sodium alcohol polyethylene glycol ether sulfosuccinate, commercially available, for example, in the form of Geropon® ACR brands (Rhodia), a3) disodium alcohol polyethylene glycol ether semisulfosuccinate, commercially available, for example, in the form of the Aerosol® brands (Cytec), the Marlinat® or Sermul® brands (Condea), the Empicol® brands (Albright&Wilson), the Secosol® brands (Stepan), the Geropon® brands (Rhodia), the Disponil® or Texapon® brands (Cognis) or the Rolpon® brands (Cesalpinia), a4) disodium N-alkylsulfosuccinamate, commercially available, for example, in the form of the Aerosol® brands (Cytec), the Rewopol® or Rewoderm® brands (Rewo), the Empimin® brands (Albright&Wilson), the Geropon® brands (Rhodia) or the Polirol® brands (Cesalpinia), a5) disodium fatty acid amide polyethylene glycol ether semisulfosuccinate, commercially available, for example, in the form of the Elfanol® or Lankropol® brands (Akzo Nobel), the Rewoderm®, Rewocid® or Rewopol® brands (Rewo), the Emcol® brands (Witco), the Standapol® brands (Cognis) or the Rolpon® brands (Cesalpinia), and a6) tetrasodium N-(1,2-dicarboxyethyl)-N-octadecylsulfosuccinamate, commercially available, for example, in the form of Aerosol 22® (Cytec).

Sulfosuccinates are commercially available, for example, as Aerosol® (Cytec), Agrilan® or Lankropol® (Akzo Nobel), Empimin® (Huntsman), Cropol® (Croda), Lutensite® (BASF), Triton® GR series (UnionCarbide), Imbirol®/Madeol®/Polirol® (Cesalpinia); as Geropon®AR series or as Geropon® SDS (Rhodia).

Preferred sulfosuccinates are, for example, the sodium, potassium and ammonium salts of bis(alkyl)sulfosuccinates, where the alkyl radicals are identical or different and contain 4 to 16 carbon atoms and are, preferably, butyl, hexyl, octyl, such as 2-ethylhexyl, or decyl radicals, which may be straight-chain or branched. Particular preference is given to sodium di($C_4$-$C_{10}$-alkyl)sulfosuccinate such as sodium di(2-ethylhexyl)sulfosuccinate.

If the oil suspension concentrates according to the invention comprise sulfosuccinates d), their proportion by weight is generally 0.5 to 60% by weight, in particular 1 to 30% by weight.

Optional agrochemically active compounds d) that may be present are, for example, agrochemically active compounds different from component a), such as herbicides, fungicides, insecticides, safeners or plant growth regulators. The agrochemically active compounds d) may be present in suspended and/or dissolved form in the organic solvent. Present in dissolved form are in particular the esters of the herbicides (B1), (B2), (B3) and (B4). From among the active compounds (C), in particular the esters of the herbicides (C2), (C3), (C6) and the safeners (S1-1) are present in dissolved form.

The inorganic salts (component e) optionally contained in the oil suspension concentrates according to the invention are preferably basic inorganic salts. These are to be understood as meaning salts which, in 1% strength aqueous solution, have a pH>7, preferably weakly basic salts having a pH between 7 and 11. Examples of such salts are carbonates, bicarbonates, hydroxides, oxides, hypochlorites and sulfites, preferably carbonates and bicarbonates. As cations, the inorganic salts preferably contain metal ions, in particular alkali metal, alkaline earth metal and transition metal ions, preferably alkali metal and alkaline earth metal ions, such as sodium, potassium, magnesium or calcium. Particularly preferred salts are alkali metal salts, in particular alkali metal carbonates and alkali metal bicarbonates, such as $Na_2CO_3$, $K_2CO_3$, $NaHCO_3$ and $KHCO_3$. The inorganic salts may be present on their own or in a mixture.

If the oil suspension concentrates according to the invention contain inorganic salts e), their proportion by weight is generally from 0.01 to 20% by weight, preferably from 0.01 to 10% by weight, particularly preferably from 0.05 to 5% by weight.

Customary auxiliaries and additives (component f) which may also be contained in the oil suspension concentrates according to the invention are, for example: surfactants, such as emulsifiers and dispersants, thickeners and thixotropic agents, wetting agents, anti-drift agents, adhesives, penetrants, preservatives and antifreeze agents, antioxidants, solubilizers, fillers, carriers and colorants, antifoams, fertilizers, evaporation inhibitors and agents which modify pH and viscosity.

Suitable emulsifiers and dispersants are, for example, non-ionic emulsifiers and dispersants, for example:

1) polyalkoxylated, preferably polyethoxylated, saturated and unsaturated aliphatic alcohols,
   having 8 to 24 carbon atoms in the alkyl radical, which is derived from the corresponding fatty acids or from petrochemical products, and
   having 1 to 100, preferably 2 to 50, ethylene oxide units (EO), it being possible for the free hydroxyl group to be alkoxylated,
   which are commercially available, for example, as Genapol® X and Genapol® O series (Clariant), Crovol® M series (Croda) or as Lutensol® series (BASF), 2) polyalkoxylated, preferably polyethoxylated, arylalkylphenols, such as, for example, 2,4,6-tris(1-phenylethyl)phenol (tristyrylphenol) having an average degree of ethoxylation of between 10 and 80, preferably from 16 to 40, such as, for example, Soprophor® BSU (Rhodia) or HOE S 3474 (Clariant), 3) polyalkoxylated, preferably polyethoxylated, alkylphenols having one or more alkyl radicals, such as, for example, nonylphenol or tri-sec-butylphenol, and a degree of ethoxylation of between 2 and 40, preferably from 4 to 15, such as, for example, Arkopal® N series or Sapogena® T series (Clariant), 4) polyalkoxylated, preferably polyethoxylated, hydroxyfatty acids or glycerides which contain hydroxyfatty acids, such as, for example, ricinine or castor oil, having a degree of ethoxylation of between 10 and 80, preferably from 25 to 40, such as, for example, the Emulsogen® EL series (Clariant) or the Agnique® CSO series (Cognis), 5) polyalkoxylated, preferably polyethoxylated, sorbitan esters, such as, for example, Atplus® 309 F (Uniqema) or the Alkamuls® series (Rhodia),
6) polyalkoxylated, preferably polyethoxylated, amines, such as, for example, Genamin® series (Clariant), Imbentin® CAM series (Kolb) or Lutensol® FA series (BASF),
7) di- and tri-block copolymers, for example from alkylene oxides, for example from ethylene oxide and propylene oxide, having average molar masses between 200 and 10 000, preferably from 1000 to 4000, g/mol, the proportion by mass of the polyethoxylated block varying between 10 and 80%, such as, for example, the Genapol® PF series (Clariant), the Pluronic® series (BASF), or the Synperonic® PE series (Uniqema).

Preferred nonionic emulsifiers and dispersants are, for example, polyethoxylated alcohols, polyethoxylated triglycerides which contain hydroxyfatty acids and polyethylene oxide/polypropylene oxide block copolymers.

If the oil suspension concentrates according to the invention contain nonionic emulsifiers and dispersants, their proportion by weight is generally from 1 to 20% by weight.

Also suitable are ionic emulsifiers and dispersants, for example:
1) polyalkoxylated, preferably polyethoxylated, emulsifiers/dispersants (cf. component e) which are ionically modified, for example by conversion of the terminal free hydroxyl function of the polyethylene oxide block into a sulfate or phosphate ester (for example as alkali metal and alkaline earth metal salts), such as, for example, Genapol® LRO or dispersant 3618 (Clariant), Emulphor® (BASF) or Crafol® AP (Cognis),
2) alkali metal and alkaline earth metal salts of alkylarylsulfonic acids having a straight-chain or branched alkyl chain, such as phenylsulfonate CA or phenylsulfonate CAL (Clariant), Atlox® 3377BM (ICI), or the Empiphos® TM series (Huntsman),
3) polyelectrolytes, such as lignosulfonates, condensates of naphthalenesulfonate and formaldehyde, polystyrenesulfonate or sulfonated unsaturated or aromatic polymers (polystyrenes, polybutadienes or polyterpenes), such as the Tamol® series (BASF), Morwet® D425 (Witco), the Kraftsperse® series (Westvaco) or the Borresperse® series (Borregard).

Preferred ionic emulsifiers/dispersants are, for example, salts of alkylarylsulfonic acids and polyelectrolytes from the polycondensation of naphthalenesulfonate and formaldehyde.

If the oil suspension concentrates according to the invention contain ionic emulsifiers and dispersants, their proportion by weight is generally from 0.1 to 20% by weight, in particular from 0.5 to 8% by weight.

If nonionic or ionic emulsifiers and dispersants are used not only because of their emulsifying/dispersing properties but also to increase the biological effectiveness, for example as penetrants or tackifiers, their proportion in the oil suspension concentrates according to the invention may be increased to up to 60% by weight.

Suitable thickeners and thixotropic agents are, for example:
1) modified natural silicates, such as chemically modified bentonites, hectorites, attapulgites, montmorillonites, smectites or other silicate minerals, such as Bentone® (Elementis), Attagel® (Engelhard), Agsorb® (Oil-Dri Corporation) or Hectorite® (Akzo Nobel),
2) synthetic silicates, such as silicates of the Sipernat®, Aerosil® or Durosil® series (Degussa), the CAB-O-SIL® series (Cabot) or the Van Gel series (R.T. Vanderbilt),
3) thickeners based on synthetic polymers, such as thickeners of the Thixin® or Thixatrol® series (Elementis),
4) thickeners based on natural polymers and natural oils, for example from the Thixin® or Thixatrol® series (Elementis).

Preferred thickeners and thixotropic agents are, for example, modified phyllosilicates and thickeners based on synthetic polymers.

If the oil suspension concentrates according to the invention contain thickeners and thixotropic agents, their proportion by weight is generally from 0.1 to 5% by weight, in particular from 0.2 to 3% by weight.

Preference is given to oil suspension concentrates according to the invention comprising:
a) 0.01 to 50% by weight, preferably 0.1 to 30% by weight, of one or more herbicides (A) und (B), in suspended form,
b) 5 to 95% by weight, preferably 20 to 80% by weight, of one or more solvents,
c) optionally 0.5 to 60% by weight, preferably 1 to 30% by weight, of one or more sulfosuccinates,
d) optionally 0.5 to 50% by weight, preferably 3 to 20% by weight, of one or more agrochemically active compounds different from a),
e) optionally 0.01 to 20% by weight, preferably 0.01 to 10% by weight, of one or more inorganic salts,
f) optionally 1 to 20% by weight of one or more nonionic emulsifiers and dispersants,
  optionally 1 to 20% by weight of one or more ionic emulsifiers and dispersants,
  optionally 0.1 to 5% by weight, preferably 0.2 to 3% by weight, of one or more thickeners and thixotropic agents.

The oil suspension concentrates according to the invention can be prepared by known processes, for example by mixing the components. Thus, it is possible, for example, to prepare a premix by adding any sulfosuccinate c) present and, if appropriate, further auxiliaries and additives f) to the organic solvent b). Any soluble agrochemically active compounds d) used are then dissolved in the premix. Once the dissolution process has ended, solid herbicide a) and, if appropriate, any insoluble active compounds d) used and also inorganic salts e) are suspended in the mixture. The coarse suspension is, if appropriate after pregrinding, subjected to fine grinding.

In another embodiment, solid herbicide a) and, if appropriate, any insoluble components d), e) and f) used are suspended in the organic solvent b) which optionally contains a sulfosuccinate c) and subjected to grinding. Any soluble active compounds d) used and any auxiliaries and additives f) which do not require grinding or are not required for the grinding process are added after grinding.

To prepare the mixtures, it is possible to use customary mixing apparatus which, if required, are thermostatted. For pregrinding, it is possible to use, for example, high-pressure homogenizers or mills operating by the rotor-stator principle, such as Ultraturrax homogenizers, for example those from IKA, or toothed colloid mills, for example from Puck. For fine grinding, it is possible to use, for example, bead mills which operate batchwise, for example from Drais, or bead mills which operate continuously, for example from Bachofen. The preparation process can be adapted to the properties of the components optionally pretreated and to technical and safety requirements and to economical considerations, and pregrinding and even fine grinding of the suspension may be dispensed with, if required.

The components a) to f) used for the preparation may comprise water as a minor component which is then also found in the oil suspension concentrates according to the invention. Accordingly, the oil suspension concentrates according to the invention may comprise small amounts of water, in general from 0 to 5% by weight. Preferably, the oil suspension concentrates according to the invention are not subjected to any drying.

For use, the oil suspension concentrates according to the invention may, if appropriate, be diluted in a customary manner (for example using water), to give, for example, suspensions, emulsions, suspoemulsions or solutions, preferably to give emulsions. It may be advantageous to add further agrochemically active compounds (for example tank mix partners in the form of corresponding formulations) and/or auxiliaries and additives customary for application, for example self-emulsifying oils, such as vegetable oils or paraffin oils, and/or fertilizers to obtained spray emulsions. Accordingly, the present invention also provides such herbicidal compositions based on the oil suspension concentrates according to the invention.

As regards further details on the formulation of crop protection products, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical formulations comprise from 0.1 to 99% by weight, in particular from 2 to 95% by weight, of active compounds of types (A) and/or (B), the following concentrations being customary depending on the type of formulation: In wettable powders, the active compound concentration is, for example, approximately 10 to 95% by weight, the remainder to 100% by weight being composed of customary formulation constituents. In the case of emulsifiable concentrates, the active compound concentration can, for example, amount to from 5 to 80% by weight. Formulations in the form of dusts generally comprise from 5 to 20% by weight of active compound, and sprayable solutions comprise approximately 0.2 to 25% by weight of active compound. In the case of granules such as dispersible granules, the active compound content depends partly on whether the active compound is in liquid or solid form and on the granulation auxiliaries and fillers which are being used. In the case of the water-dispersible granules, the content is generally between 10 and 90% by weight. In the case of oil suspension concentrates, the active compound concentration is generally from 0.01 to 50% by weight.

In addition, the abovementioned active compound formulations may comprise, if appropriate, the conventional adhesives, wetting agents, dispersants, emulsifiers, preservatives, antifreeze agents, solvents, fillers, colorants, carriers, antifoams, evaporation inhibitors, pH regulators or viscosity regulators.

The herbicidal action of the herbicide combinations according to the invention can be improved, for example, by surfactants, preferably by wetting agents from the group of the fatty alcohol polyglycol ethers. The fatty alcohol polyglycol ethers preferably contain 10-18 carbon atoms in the fatty alcohol radical and 2-20 ethylene oxide units in the polyglycol ether moiety. The fatty alcohol polyglycol ethers can be nonionic or ionic, for example in the form of fatty alcohol polyglycol ether sulfates, which are used, for example, as alkali metal salts (e.g. sodium salts or potassium salts) or ammonium salts, but also as alkaline earth metal salts such as magnesium salts, such as sodium $C_{12}/C_{14}$-fatty alcohol diglycol ether sulfate (Genapol® LRO, Clariant GmbH); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, ($C_{10}$-$C_{18}$)-, preferably ($C_{10}$-$C_{14}$)-fatty alcohol polyglycol ethers containing 2-20, preferably 3-15, ethylene oxide units (e.g. isotridecyl alcohol polyglycol ether), such as Genapol® X-030, Genapol® X-060, Genapol® X-080 or Genapol® X-150 (all from Clariant GmbH). The present invention furthermore embraces the combination of compounds of the formula (I) and their salts with the wetting agents mentioned above from the group of the fatty alcohol polyglycol ethers which preferably contain 10-18 carbon atoms in the fatty alcohol radical and 2-20 ethylene oxide units in the polyglycol ether moiety and which can be present in nonionic or ionic form (for example as fatty alcohol polyglycol ether sulfates). Preference is given to $C_{12}/C_{14}$-fatty alcohol diglycol ether sulfate sodium (Genapol® LRO, Clariant GmbH) and isotridecyl alcohol polyglycol ether having 3-15 ethylene oxide units, for example from the Genapol® X series, such as Genapol® X-030, Genapol® X-060, Genapol® X-080 and Genapol® X-150 (all from Clariant GmbH). Moreover, it is known that fatty alcohol polyglycol ethers such as nonionic or ionic fatty alcohol polyglycol ethers (for example fatty alcohol polyglycol ether sulfates) are also suitable as penetrants and synergists for a number of other herbicides, inter alia also for herbicides from the group of the imidazolinones (see, for example, EP-A-0502014).

The herbicidal effect of the herbicide combinations according to the invention can also be increased using vegetable oils. The term vegetable oils is to be understood as meaning oils from oil-plant species, such as soybean oil, rapeseed oil, corn oil, sunflower oil, cottonseed oil, linseed oil, coconut oil, palm oil, safflower oil or castor oil, in particular rapeseed oil, and their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-fatty acids. The $C_{10}$-$C_{22}$-fatty acid esters are, for example, esters of unsaturated or saturated $C_{10}$-$C_{22}$-fatty acids, in particular those with an even number of carbon atoms, for example erucic acid, lauric acid, palmitic acid and, in particular, $C_{18}$-fatty acids such as stearic acid, oleic acid, linoleic acid or linolenic acid.

Examples of $C_{10}$-$C_{22}$-fatty acid esters are esters obtained by reacting glycerol or glycol with the $C_{10}$-$C_{22}$-fatty acids as they exist, for example in oils from oil-plant species, or $C_1$-$C_{20}$-alkyl-$C_{10}$-$C_{22}$-fatty acid esters as can be obtained, for example, by transesterification of the abovementioned glycerol- or glycol-$C_{10}$-$C_{22}$-fatty acid esters with $C_1$-$C_{20}$-alcohols (for example methanol, ethanol, propanol or butanol). Transesterification can be carried out by known methods as are described, for example, in Römpp Chemie Lexikon, 9th edition, volume 2, page 1343, Thieme Verlag Stuttgart.

Preferred $C_1$-$C_{20}$-alkyl-$C_{10}$-$C_{22}$-fatty acid esters are the methyl, ethyl, propyl, butyl, 2-ethylhexyl and dodecyl esters. Preferred glycol- and glycerol-$C_{10}$-$C_{22}$-fatty acid esters are the uniform or mixed glycol esters and glycerol esters of $C_{10}$-$C_{22}$-fatty acids, in particular those fatty acids which have an even number of carbon atoms, for example erucic acid, lauric acid, palmitic acid and, in particular, $C_{18}$-fatty acids such as stearic acid, oleic acid, linoleic acid or linolenic acid.

The vegetable oils can be present in the herbicidal compositions according to the invention for example in the form of commercially available oil-containing formulation additives, in particular those based on rapeseed oil such as Hasten® (Victorian Chemical Company, Australia, hereinbelow termed Hasten, main constituent: rapeseed oil ethyl ester), Actirob®B (Novance, France, hereinbelow termed ActirobB, main constituent: rapeseed oil methyl ester), Rako-Binol® (Bayer AG, Germany, termed Rako-Binol hereinbelow, main constituent: rapeseed oil), Renol® (Stefes, Germany, termed Renol hereinbelow, vegetable oil constituent: rapeseed oil methyl ester), or Stefes Mero® (Stefes, Germany, hereinbelow termed Mero, main constituent: rapeseed oil methyl ester).

For use, the formulations, which are present in commercially available form, are optionally diluted in the customary manner, for example using water. Preparations in the form of dusts, soil granules, granules for broadcasting and sprayable solutions are usually not diluted further with other inert substances prior to use.

The active compounds can be applied to the plants, parts of the plants, seeds of the plants or the area on which the plants grow, for example the pasture area or the area under cultivation, preferably to the green plants and parts of the plants and, if appropriate, additionally to the soil.

One possible use is the joint application of the active compounds in the form of tank mixes, the concentrated formulations of the individual active compounds, in optimal formulations, jointly being mixed with water in the tank and the resulting spray mixture being applied.

A joint herbicidal formulation of the combination according to the invention of the active compounds (A) and (B) has the advantage of being easier to apply since the quantities of the components are already presented in the correct ratio to each other. Moreover, the adjuvants in the formulation can be matched optimally to each other.

A. General Formulation Examples a) A dust is obtained by mixing 10 parts by weight of an active compound/active compound mixture and 90 parts by weight of talc as inert material and comminuting the mixture in a hammer mill.

b) A wettable powder which is readily dispersible in water is obtained by mixing 25 parts by weight of an active compound/active compound mixture, 64 parts by weight of kaolin-containing quartz as inert material, 10 parts by weight of potassium lignosulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (® Triton X 207), 3 parts by weight of isotridecanol polyglycol ether (8 EO) and 71 parts by weight of paraffinic mineral oil (boiling range for example approx. 255 to 277° C.), and grinding the mixture in a ball mill to a fineness of below 5 microns.

d) An emulsifiable concentrate is obtained from 15 parts by weight of an active compound/active compound mixture, 75 parts by weight of cyclohexanone as solvent and 10 parts by weight of oxyethylated nonylphenol as emulsifier.

e) Water-dispersible granules are obtained by mixing
   75 parts by weight of an active compound/active compound mixture,
   10 parts by weight of calcium lignosulfonate,
   5 parts by weight of sodium lauryl sulfate,
   3 parts by weight of polyvinyl alcohol and
   7 parts by weight of kaolin,
   grinding the mixture on a pinned-disk mill and granulating the powder in a fluidized bed by spraying on water as granulation liquid.

f) Water-dispersible granules are also obtained by homogenizing and precomminuting, in a colloid mill,
   25 parts by weight of an active compound/active compound mixture,
   5 parts by weight of sodium 2,2'-dinaphthylmethane-6,6'-disulfonate,
   2 parts by weight of sodium oleoylmethyltaurinate,
   1 part by weight of polyvinyl alcohol,
   17 parts by weight of calcium carbonate and
   50 parts by weight of water,
   subsequently grinding the mixture in a bead mill and atomizing and drying the resulting suspension in a spray tower by means of a single-substance nozzle.

B. Biological Examples

1. Herbicidal Action Against Weeds (Greenhouse Trials)

The seeds or rhizome pieces of typical harmful plants were placed into sandy loam soil in round pots, size 13, covered with soil and grown in a greenhouse under good growth conditions. After the harmful plants had emerged, they were treated, as a rule at the 2- to 3-leaf stage, with various dosages of the compositions according to the invention at a water application rate of 100 to 400 I/ha (converted).

After the treatment (approx. 4 weeks after application), the herbidical activity of the active compounds or active compound mixtures was scored visually by comparing the treated plants with untreated controls. Damage and development of all above-ground parts of the plants was recorded. Scoring was done on a percentage scale (100% action=all plants dead; 50% action=50% of the plants and green plant parts dead; 0% action=no discernible action).

The results are listed in the tables below, where the activity measured for the independent use of the active compounds (A) and (B) is stated in brackets.

TABLE 1

| Active compound(s) | Application rate g of ai/ha | Veronica persica % activity | Lamium amplexicaule % activity |
|---|---|---|---|
| A) Amidosulfuron | 20 | 20 | 18 |
| B) Picloram | 60 | 62 | 75 |
| A) + B) | 20 + 60 | 100 (20 + 62) | 100 (18 + 75) |

2. Herbicidal Action Against Woody Shrub Weeds (Greenhouse Trials)

The plants were cultivated to the 5- to 6-leaf stage. Herbicide application and scoring of the trial were carried out as in Example 1.

TABLE 2

| Active compound(s) | Application rate g of ai/ha | Acacia farnesiana % activity | Mimosa pigra % activity |
|---|---|---|---|
| A) Amidosulfuron | 40 | 43 | 20 |
| B) Aminopyralid | 60 | 55 | 73 |
| A) + B) | 40 + 60 | 100 (43 + 55) | 100 (20 + 73) |

The invention claimed is:

1. A herbicide combination comprising components (A) and (B), where
   (A) denotes at least one herbicide selected from the group consisting of compounds of formula (I) and salts thereof

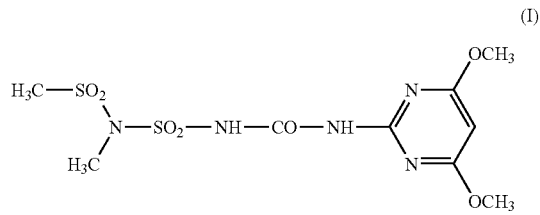 [SMILES: COc1cc(OC)nc(NC(=O)NS(=O)(=O)N(C)S(C)(=O)=O)n1]

(I)

and
   (B) denotes at least one herbicide selected from the group consisting of (B1) picloram and salts and esters thereof, and (B2) aminopyralid and salts and esters thereof, wherein the ratio of A:B1 is 1:1 to 1:50, and wherein the ratio of A:B2 is 1:1 to 1:20.

2. The herbicide combination as claimed in claim 1 which comprises, as component (A), at least one herbicide selected from the group consisting of amidosulfuron and amidosulfuron-sodium.

3. The herbicide combination as claimed in claim 1, additionally comprising at least one or further component selected from the group consisting of agrochemically active compounds, formulation auxiliaries and additives suitable for use in crop protection.

4. The herbicide combination as claimed in claim 1, additionally comprising at least one safener and/or herbicide different from components (A) and (B).

5. The herbicide combination as claimed in of claim 1, additionally comprising at least one active compound selected from the group consisting of iodosulfuron and salts and esters thereof, mefenpyr and salts and esters thereof, bromoxynil and salts and esters thereof, ioxynil and salts and esters thereof, metribuzin, propoxycarbazone and salts and esters thereof, ethofumesate, diflufenican and ethoxysulfuron and salts and esters thereof.

6. A method for controlling harmful plants which comprises applying a synergistic herbicide combination jointly or separately to plants, plant parts, plant seeds and/or an area on which plants grow,
wherein the herbicide combination comprises components (A) and (B), where
(A) denotes at least one herbicide selected from the group consisting of compounds of formula (I) and salts thereof

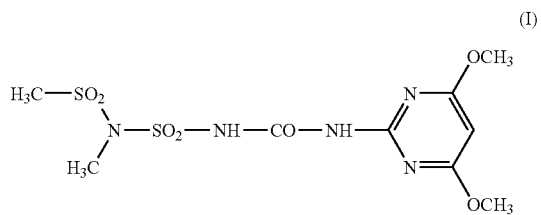

(I)

and
(B) denotes at least one herbicide selected from the group consisting of (B1) picloram and salts and esters thereof, and B2 aminopyralid and salts and esters thereof wherein the application rate ratio of A:B1 is 1:1 to 1:50, and wherein the application rate ratio of A:B2 is 1:1 to 1:20.

7. The method as claimed in claim 6 for the selective control of harmful plants in plant crops.

8. The method as claimed in claim 7 for the control of harmful plants in monocotyledonous plant crops.

9. The method as claimed in claim 7 in which the plant crops are genetically modified and/or have been obtained by mutation/selection.

10. The synergistic herbicide combination as defined in claim 1 for controlling harmful plants.

11. The method as claimed in claim 7 for the control of harmful plants in pasture crops.

12. The synergistic herbicide combination as claimed in claim 1, wherein component (B) is selected from the group consisting of picloram and salts and esters thereof.

13. The synergistic herbicide combination as claimed in claim 1, wherein component (B) is selected from the group consisting of aminopyralid and salts and esters thereof.

14. The method as claimed in claim 6, wherein B comprises B1 and the application rate ratio of A:B1 is 1:1 to 1:50.

15. The method of claimed in claim 6, wherein B comprises B1 and the application rate ratio of A:B1 is 1:2 to 1:10.

16. The method as claimed in claim 6, wherein B comprises B2 and the application rate ratio of A:B2 is 1:1 to 1:20.

17. The method as claimed in claim 6, wherein B comprises B2 and the application rate ratio of A:B2 is 1:1 to 1:5.

18. The synergistic herbicide combination as claimed in claim 1, wherein component (B) is selected from the group consisting of picloram, picloram-dimethylammonium, picloram-isoctyl, picloram-sodium, picloram-potassium, picloram-triisopropanolammonium, picloram-triethanolammonium, and picloram-triisopropylammonium.

19. The synergistic herbicide combination as claimed in claim 1, wherein component (B) is selected from the group consisting of aminopyralid, aminopyralid-sodium, aminopyralid-potassium, and aminopyralid-tri(2-hydroxypropyl) ammonium.

20. The method of claim 7, wherein the harmful plants are selected from the group consisting of *Pharbitis purpurea*, *Veronica persica*, and *Mimosa pigra*.

* * * * *